(12) United States Patent
Sainz et al.

(10) Patent No.: US 7,098,378 B2
(45) Date of Patent: Aug. 29, 2006

(54) TRANSGENIC PLANTS COMPROMISING NUCLEIC ACID MOLECULES ENCODING RAR1 DISEASE RESISTANCE PROTEINS AND USES THEREOF

(75) Inventors: Manuel B. Sainz, Durham, NC (US); John Salmeron, Hillsborough, NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 11/011,906

(22) Filed: Dec. 14, 2004

(65) Prior Publication Data

US 2005/0160491 A1    Jul. 21, 2005

Related U.S. Application Data

(62) Division of application No. 10/305,770, filed on Nov. 27, 2002, now Pat. No. 6,956,115.

(60) Provisional application No. 60/334,348, filed on Nov. 30, 2001.

(51) Int. Cl.
| | |
|---|---|
| C12N 15/09 | (2006.01) |
| C12N 15/29 | (2006.01) |
| C12N 15/82 | (2006.01) |
| A01H 5/00 | (2006.01) |
| A01H 5/10 | (2006.01) |

(52) U.S. Cl. .................... 800/279; 800/278; 800/298; 800/295; 800/317; 800/320.1; 435/69.1; 435/468

(58) Field of Classification Search ................ 800/278, 800/279, 298, 295, 317, 320.1; 435/69.1, 435/468
See application file for complete search history.

(56) References Cited

U.S. PATENT DOCUMENTS

2001/0047521 A1   11/2001   Crane et al.

FOREIGN PATENT DOCUMENTS

| WO | WO00/08160 | 2/2000 |
|---|---|---|
| WO | WO 00/08160 | * 2/2000 |

OTHER PUBLICATIONS

Depicker, A. and Montagu, M.V., *Post-transcriptional gene silencing in plants* Current Opinion in Cell Biology, vol. 9 (1997), p. 373-382.
Muskett, P.R. et al., *Arabidopsis RAR1 exerts rate-limiting control of R gene-mediated defenses against multiple pathogens*, The Plant Cell 14:979-992 (May 2002).
Sasaki, T. NCBI [online] *Rice cDNA from callus 1997* Accession No. C28356, Aug. 6, 1997.
Shirasu et al, *A Novel Class of Eukaryotic Zinc-Binding Proteins Is Required for Disease Resistance Signaling in Barley and Development in C. elegans* Cell, vol. 99 (Nov. 12, 1999), pp. 355-366.
Tornero, P. et al., *RAR1 and NDR1 contribute quantitatively to Disease resistance in Arabidopsis, and their relative contributions are dependent on the R gene assayed*, The Plant Cell 14:1005-1015 (May 2002).
Xie, G.L. and Mew, T.W., *A Leaf Inoculation Method for Detection Plant Disease* (Sep. 1998), pp. 1007-1011.

* cited by examiner

*Primary Examiner*—Medina A. Ibrahim
(74) *Attorney, Agent, or Firm*—Syngenta Participations AG

(57) ABSTRACT

The present invention pertains to transgenic plants comprising nucleic acid molecules comprising nucleotide sequences that encode RAR1 proteins involved in disease resistance, and the RAR1 polypeptides. The invention particularly relates to methods of altering the expressing nucleic acid molecules encoding RAR1 proteins in transgenic plants to alter the level disease resistance, and to transgenic plants, progeny and seed therefrom, having altered enhanced disease resistance. The invention further relates to methods of enhancing expression of R resistance genes, disease resistance signal transduction genes, genes involved in mediating disease resistance or involved in the synthesis of molecules mediating disease resistance. The invention also relates to methods of regulating the expression of other coding sequences of interest by increasing the expression of the nucleic acid molecules of the invention.

15 Claims, 2 Drawing Sheets

SEQUENCE LISTING

```
<160> NUMBER OF SEQ ID NOS: 5

<210> SEQ ID NO 1
<211> LENGTH: 702
<212> TYPE: DNA
<213> ORGANISM: Oryza sativa

<400> SEQUENCE: 1
atgtcgacgg aggcggagac caccagcgcc gccgccccg ccccgcccc cgccccgca      60 tcggcgccgg cgcggtgcca gcggataggc tgcgacgcca cgttcaccga cgacaacaac    120
cccgacggct cctgccaata ccaccctcc ggacctatgt ttcatgatgg catgaaacag    180
tggagttgct gtaagcaaaa aagccatgat tttagcctat ttttggctat tcctgggtgc    240
aaaactggaa agcacacaac tgagaaacca atcacaaaag cagttcctac taaaccatca    300
aaggcagttc cagtccagac ttcgaagcag agtgtgggag ctgacacttg ctcaaggtgc    360
cgtcaaggtt tcttttgctc tgaccatgga tcacaaccca aggcacaaat accaaccgct    420
accagtgata ctaacatggt acctgttgag aagcctgcag ttccaccacc aaagaaaaaa    480
attgatctga atgagcctag ggtttgtaag aacaaaggat gtggtaaaac ctacaaggag    540
aaggataatc atgatgaagc atgcgattac catccaggac ctgcagtttt tcgcgacagg    600
attagagggt ggaaatgttg tgatattcat gtcaaggaat ttgatgaatt tatggagatc    660
cctccgtgca caaagggttg gcacaatgct gatgccgcat ga                      702

<210> SEQ ID NO 2
<211> LENGTH: 233
<212> TYPE: PRT
<213> ORGANISM: Oryza sativa

<400> SEQUENCE: 2

Met Ser Thr Glu Ala Glu Thr Thr Ser Ala Ala Ala Pro Ala Pro Ala
1               5                  10                  15

Pro Ala Pro Ala Ser Ala Pro Ala Arg Cys Gln Arg Ile Gly Cys Asp
                20                  25                  30

Ala Thr Phe Thr Asp Asp Asn Asn Pro Asp Gly Ser Cys Gln Tyr His
            35                  40                  45

Pro Ser Gly Pro Met Phe His Asp Gly Met Lys Gln Trp Ser Cys Cys
        50                  55                  60
```

Lys Gln Lys Ser His Asp Phe Ser Leu Phe Leu Ala Ile Pro Gly Cys
 65                  70                  75                  80

Lys Thr Gly Lys His Thr Thr Glu Lys Pro Ile Thr Lys Ala Val Pro
                 85                  90                  95

Thr Lys Pro Ser Lys Ala Val Pro Val Gln Thr Ser Lys Gln Ser Val
            100                 105                 110

Gly Ala Asp Thr Cys Ser Arg Cys Arg Gln Gly Phe Phe Cys Ser Asp
        115                 120                 125

His Gly Ser Gln Pro Lys Ala Gln Ile Pro Thr Ala Thr Ser Asp Thr
130                 135                 140

Asn Met Val Pro Val Glu Lys Pro Ala Val Pro Pro Lys Lys
145                 150                 155                 160

Ile Asp Leu Asn Glu Pro Arg Val Cys Lys Asn Lys Gly Cys Gly Lys
                165                 170                 175

Thr Tyr Lys Glu Lys Asp Asn His Asp Glu Ala Cys Asp Tyr His Pro
            180                 185                 190

Gly Pro Ala Val Phe Arg Asp Arg Ile Arg Gly Trp Lys Cys Cys Asp
        195                 200                 205

Ile His Val Lys Glu Phe Asp Glu Phe Met Glu Ile Pro Pro Cys Thr
210                 215                 220

Lys Gly Trp His Asn Ala Asp Ala Ala
225                 230

<210> SEQ ID NO 3
<211> LENGTH: 23
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(23)
<223> OTHER INFORMATION: Oryza sativa

<400> SEQUENCE: 3
aagacgaaga tgtcgacgga ggc                                    23

<210> SEQ ID NO 4
<211> LENGTH: 21
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(21)
<223> OTHER INFORMATION: Oryza sativa

<400> SEQUENCE: 4
tcatgcggca tcagcattgt g                                      21

<210> SEQ ID NO 5
<211> LENGTH: 5
<212> TYPE: PRT
<213> ORGANISM: artificial sequence
<220> FEATURE:
<221> NAME/KEY: misc_feature
<222> LOCATION: (1)..(5)

```
<223> OTHER INFORMATION: epitope tag

<400> SEQUENCE: 5

Phe His His Thr Thr
1               5
```

TRANSGENIC PLANTS COMPROMISING NUCLEIC ACID MOLECULES ENCODING RAR1 DISEASE RESISTANCE PROTEINS AND USES THEREOF

This application is a divisional of U.S. application Ser. No. 10/305,770, filed Nov. 27, 2002, now U.S. Pat. No. 6,956,115 which claims the benefit of U.S. Provisional Patent Application No. 60/334,348 filed Nov. 30, 2001, both of which are hereby incorporated by reference in their entirety.

FIELD OF THE INVENTION

The present invention pertains to nucleic acid molecules isolated from *Oryza sativa* comprising nucleotide sequences that encode RAR1 proteins involved in disease resistance, and the RAR1 polypeptides. The invention particularly relates to methods of altering the expressing nucleic acid molecules encoding RAR1 proteins in transgenic plants to alter the level disease resistance, and to transgenic plants, progeny and seed therefrom, having altered enhanced disease resistance. The invention further relates to methods of enhancing expression of R resistance genes, disease resistance signal transduction genes, genes involved in mediating disease resistance or involved in the synthesis of molecules mediating disease resistance. The invention also relates to methods of regulating the expression of other coding sequences of interest by increasing the expression of the nucleic acid molecules of the invention. The invention also relates to methods of cloning nucleic acid molecules encoding RAR1 proteins using polymerase chain reaction and primers of the invention.

BACKGROUND OF THE INVENTION

Crops are biological monocultures under severe disease pressure from pathogenic bacteria, fungi and viruses. Cereal crops are the primary source of food for humans and their animals. The yield loss due to cereal plant diseases varies by crop, season and locale, but is estimated to exceed $100 billion worldwide (Brears and Ryals (1994) Agro-Food-Industry Hi-Tech Jul./Aug. 10–13). Two major approaches to solve the problem are pesticide applications and the use of resistant germplasm. The source of this resistant is often wild species related to the crop plant (exotics), and such genes are introduced into new crop cultivars by laborious and time-consuming genetic backcrossing, to retain the favorable characteristics of the crop parent.

Effective genetic disease resistance in plants is governed by resistance (R) genes. Historically, introgressed exotic germplasm conferring disease resistance has been found to contain novel plant R genes. Plant R genes confer resistance to pathogen races bearing a cognate avirulence (avr) gene. The absence of either member of a cognate R/avr gene pair can result in disease. There are multiple R/avr cognate gene pairs in the plant and the pathogen, respectively, varying in the strength of the defense response they elicit.

The RAR1 gene of barley functions in disease resistance mediated by a subset of R genes (Peterhansel et al. (1997) Plant Cell 9: 1397–1409). RAR1 has been cloned and encodes a protein with two novel Zn-binding (named CHORD) domains (Shirasu et al. (1999) Cell 99:355–366). This group also reported highly conserved RAR1 homologs in humans, *Caenorhabitis elegans*, *Drosophila melanogaster*, as well as in the model dicot *Arabidopsis thaliana*.

Given the high degree of genomic synteny between cereals (Devos and Gale (2000) Plant Cell 12: 637–646), we reasoned that a full-length rice RAR1 gene should both exist and function in disease resistance in that species. Using our proprietary rice genomic database, a single rice RAR1 cDNA was cloned. The gene functions in mediating resistance by a subset of R genes in response to certain pathogen races. Over-expression of RAR1 confers enhanced disease resistance by mechanisms which are currently unclear.

SUMMARY OF THE INVENTION

The present invention relates to a novel cDNA sequence of the RAR1 gene from rice, the polypeptide and nucleic acid molecules encoding the polypeptide sequence, and to methods of use thereof. Further the invention relates to transgenic plants comprising a RAR1 nucleic acid, and transgenic plants having enhanced resistance to disease. Preferably, the RAR1 nucleic acid is from rice.

This Summary of Invention lists several embodiments of the invention, and in many cases lists variations and permutations of these embodiments. This Summary is merely exemplary of the numerous and varied embodiments. Mention of one or more preferred features of a given embodiment is likewise exemplary. Such embodiment can typically exist with or without the feature(s) mentioned; likewise, those features can be applied to other embodiments of the invention, whether listed in this Summary or not. To avoid excessive repetition, this Summary does not list or suggest all possible combinations of such features.

Embodiments of the present invention relate to an isolated nucleic acid molecule comprising:
 a) an isolated nucleic acid molecule encoding an amino acid sequence of SEQ ID NO:2, and conservatively modified and polymorphic variants thereof;
 b) an isolated nucleic acid molecule which selectively hybridizes at high stringency to a nucleic acid molecule of (a);
 c) complementary sequence of nucleic acid molecules of (a) or (b);
 d) an isolated nucleic acid molecule which is the reverse complement of (a), (b) or (c);
 e) an isolated nucleic molecule encoding a functional portion of the polypeptide of SEQ ID NO:2.

Embodiments of the invention also relate to an isolated nucleic acid molecule wherein the nucleotide sequence comprises:
 a) a nucleotide sequence of SEQ ID NO:1, fragment, domain or feature thereof;
 b) a nucleotide sequence having substantial similarity to (a);
 c) a nucleotide sequence capable of selectively hybridizing at high stringency to (a);
 d) a nucleotide sequence complementary to (a), (b) or (c);
 e) a nucleotide sequence which is the reverse complement of (a), (b) or (c).

Embodiments of the present invention also contemplate an expression cassette including a promoter sequence operably linked to an isolated nucleic acid of the present invention. The expression cassette may further comprise a terminator.

Further encompassed within the invention is a recombinant vector comprising an expression cassette according to embodiments of the present invention.

Also encompassed are cells, which comprise nucleic acid molecules or expression cassettes, according to the present disclosure. The cells may be bacterial, fungal, yeast, plant or animal cells.

Preferably, the cells are plant cells, and plants comprising these plant cells. In a preferred embodiment, the plant is a dicot. In another preferred embodiment, the plant is a gymnosperm. In another preferred embodiment, the plant is a monocot. In a more preferred embodiment, the monocot is a cereal. In a more preferred embodiment, the cereal may be, for example, maize, wheat, barley, oats, rye, millet, sorghum, triticale, secale, einkorn, spelt, emmer, teff, milo, flax, gramma grass, *Tripsacum* and teosinte. In a most preferred embodiment, the cereal is rice.

The transgenic plants are selected from the group consisting of: rice, wheat, barley, rye, corn, potato, canola, soybean, sunflower, carrot, sweet potato, sugarbeet, bean, pea, chicory, lettuce, cabbage, cauliflower, broccoli, turnip, radish, spinach, asparagus, onion, garlic, eggplant, pepper, celery, squash, pumpkin, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum and sugarcane.

The present invention relates to a transgenic plant comprising the expression cassette according to the invention, and to the progeny and seeds from the transgenic plant.

In one embodiment, the expression cassette is expressed throughout the plant. In another embodiment, the expression cassette is expressed in a specific location or tissue of a plant. In a more preferred embodiment, the location or tissue is for example, but not limited to, epidermis, vascular tissue, meristem, cambium, cortex or pith. In a most preferred embodiment, the location or tissue is leaf or sheath, root, flower, and developing ovule or seed.

In another embodiment, the invention relates to a transgenic plant comprising the nucleic acid molecule of the invention and to progeny and seed from the transgenic plant.

In one embodiment, the invention relates to the vector pNOV6605 having the Accession No. NRRL B-30635; the vector pNOV5352 or the vector p11182.

The invention further relates to a method of enhancing pathogen or disease resistance in a plant, comprising expressing an expression cassette comprising a RAR1 encoding nucleic acid molecule from any plant or the expression cassette according to the invention. In particular embodiments, the pathogen or disease is a nematode, bacteria, fungus, virus or viroid. In more particular embodiments, the disease is selected from the group consisting of: *Xanthomonas* spp., *Psudomonas* spp., *Rhizoctonia* spp., *Magnaporthe* spp., *Pythium* spp., *Phytophthora* spp., *Fusarium* spp. *Sclerotinia* spp. In another embodiment, the plant produced by the method has enhanced pathogen or disease resistance.

In one embodiment, the invention provides a method of increasing expression of R disease resistance genes in a plant, comprising the step of expressing an expression cassette comprising a RAR1 encoding nucleic acid molecule from any plant or the expression cassette of the invention in a plant.

In another embodiment, the invention provides a method of increasing the expression of a coding sequence of interest comprising the steps of: expressing an expression cassette comprising an RAR1-regulated promoter and a coding sequence of interest in the transgenic plant according to the invention. A coding sequence of interest can be any nucleotide sequence for producing a desired gene product. For example, a coding sequence can be, but is not limited to, a herbicide tolerance, an insecticidal, a disease resistance, abiotic stress tolerance, grain quality trait, or yield quality coding region.

An embodiment of the invention is an isolated nucleic acid molecule comprising the sequence of SEQ ID NO: 3 or 4. The invention also relates to a method of isolating a RAR1 homologue involved R gene expression leading to disease resistance in plants comprising the step of amplifying a nucleic acid molecule from a plant DNA library using the polymerase chain reaction with a pair of primers corresponding to the first 20 nucleotides of SEQ ID NO: 1 and the reverse complement of the last 20 nucleotides of SEQ ID NO:1 or using at least one isolated nucleic acid molecule of SEQ ID NO:3 or 4. The invention further relates to the isolated nucleic acid molecule amplified by the method, wherein the molecule encodes a polypeptide that enhances disease resistance when expressed in a plant.

The invention also provides a polypeptide comprising:
  a) a polypeptide sequence of SEQ ID NO:2;
  b) a polypeptide sequence having substantial similarity to (a);
  c) a polypeptide sequence encoded by a nucleotide sequence identical or substantially similar to a nucleotide sequence of SEQ ID NO:1;
  d) a polypeptide sequence encoded by a nucleic acid molecule capable of hybridizing under high stringency conditions to a nucleic acid molecule listed in SEQ ID NO:1 or to a sequence complementary thereto; and
  e) a functional fragment of (a), (b), (c) or (d).

The invention also provides a method of producing a polypeptide of claim 25, comprising the steps of:
  a) growing recombinant cells comprising an expression cassette under suitable growth conditions, the expression cassette comprising a nucleic acid molecule of claim 1; and
  b) isolating the polypeptide from the recombinant cells.

In one embodiment, the invention relates to a method of decreasing the expression of a RAR1 homologue in a plant comprising:
  (a) expressing in said plant a DNA molecule of the invention or a portion thereof in "sense" orientation; or
  (b) expressing in said plant a DNA molecule of the invention or a portion thereof in "anti-sense" orientation; or
  (c) expressing in said plant a ribozyme capable of specifically cleaving a messenger RNA transcript encoded by an endogenous gene corresponding to a DNA molecule of the invention; or
  (d) expressing in a plant an aptamer specifically directed to a protein encoded by a DNA molecules of the invention; or
  (e) expressing in a plant a mutated or a truncated form of a DNA molecule of the invention;
  (f) modifying by homologous recombination in a plant at least one chromosomal copy of the gene corresponding to a DNA molecule of the invention; or
  g) modifying by homologous recombination in a plant at least one chromosomal copy of the regulatory elements of a gene corresponding to any one of the DNA molecules of the invention; or
  h) expressing in said plant a DNA molecule of the invention or a portion thereof in the "sense" and "antisense" orientation.

One embodiment of the invention is a plant made by a method of a-h, wherein the plant has decreased RAR1 expression compared to a parental plant. Preferably, the plant has decreased disease resistance.

Another embodiment is an antibody cross-reactive to the polypeptide of SEQ ID NO:2 or variant thereof.

In one embodiment, a transgenic plant comprising the expression cassette has increased or decreased disease resistance. In another preferred embodiment, the the expression of the nucleic acid molecule of the invention is modified by overexpression, underexpression, antisense modulation, sense suppression, inducible expression, inducible repression, dsRNA interference, or inducible modulation.

BRIEF DESCRIPTION OF THE SEQUENCES IN THE SEQUENCE LIST

Figure 1:
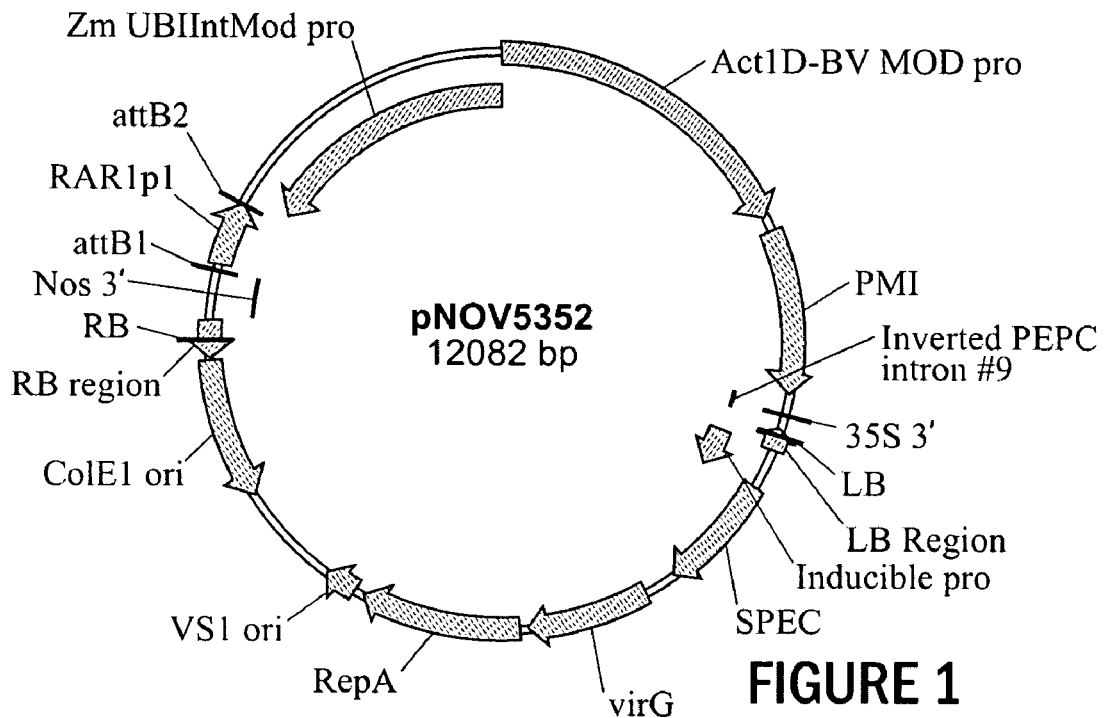
FIG. 1 is a map of plasmid pNOV5352.

SEQ ID NO:1 is the nucleotide sequence isolated from Oryza sativa of the RAR1 gene.
SEQ ID NO: 2 is the amino acid sequence encoded by SEQ ID NO:1.
SEQ ID NO:3 is the nucleotide sequence of Primer RAR1-ATG.
SEQ ID NO:4 is the nucleotide sequence of Primer RAR1-TGA.

Definitions

For clarity, certain terms used in the specification are defined and presented as follows:

"Associated with/operatively linked" refer to two nucleic acid sequences that are related physically or functionally. For example, a promoter or regulatory DNA sequence is said to be "associated with" a DNA sequence that codes for an RNA or a protein if the two sequences are operatively linked, or situated such that the regulator DNA sequence will affect the expression level of the coding or structural DNA sequence.

A "chimeric construct" is a recombinant nucleic acid sequence in which a promoter or regulatory nucleic acid sequence is operatively linked to, or associated with, a nucleic acid sequence that codes for an mRNA or which is expressed as a protein, such that the regulatory nucleic acid sequence is able to regulate transcription or expression of the associated nucleic acid sequence. The regulatory nucleic acid sequence of the chimeric construct is not normally operatively linked to the associated nucleic acid sequence as found in nature.

Co-factor: natural reactant, such as an organic molecule or a metal ion, required in an enzyme-catalyzed reaction. A co-factor is e.g. NAD(P), riboflavin (including FAD and FMN), folate, molybdopterin, thiamin, biotin, lipoic acid, pantothenic acid and coenzyme A, S-adenosylmethionine, pyridoxal phosphate, ubiquinone, menaquinone. Optionally, a co-factor can be regenerated and reused.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

Complementary: "complementary" refers to two nucleotide sequences that comprise antiparallel nucleotide sequences capable of pairing with one another upon formation of hydrogen bonds between the complementary base residues in the antiparallel nucleotide sequences.

Enzyme activity: means herein the ability of an enzyme to catalyze the conversion of a substrate into a product. A substrate for the enzyme comprises the natural substrate of the enzyme but also comprises analogues of the natural substrate, which can also be converted, by the enzyme into a product or into an analogue of a product. The activity of the enzyme is measured for example by determining the amount of product in the reaction after a certain period of time, or by determining the amount of substrate remaining in the reaction mixture after a certain period of time. The activity of the enzyme is also measured by determining the amount of an unused co-factor of the reaction remaining in the reaction mixture after a certain period of time or by determining the amount of used co-factor in the reaction mixture after a certain period of time. The activity of the enzyme is also measured by determining the amount of a donor of free energy or energy-rich molecule (e.g. ATP, phosphoenolpyruvate, acetyl phosphate or phosphocreatine) remaining in the reaction mixture after a certain period of time or by determining the amount of a used donor of free energy or energy-rich molecule (e.g. ADP, pyruvate, acetate or creatine) in the reaction mixture after a certain period of time.

Expression Cassette: "Expression cassette" as used herein means a nucleic acid molecule capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular DNA sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue or organ or stage of development.

Gene: the term "gene" is used broadly to refer to any segment of DNA associated with a biological function. Thus, genes include coding sequences and/or the regulatory sequences required for their expression. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

Heterologous/exogenous: The terms "heterologous" and "exogenous" when used herein to refer to a nucleic acid sequence (e.g. a DNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" nucleic acid (e.g. DNA) sequence is a nucleic acid (e.g. DNA) sequence naturally associated with a host cell into which it is introduced.

Hybridization: The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

Inhibitor: a chemical substance that inactivates the enzymatic activity of a protein such as a biosynthetic enzyme, receptor, signal transduction protein, structural gene product, or transport protein. The term "herbicide" (or "herbicidal compound") is used herein to define an inhibitor applied to a plant at any stage of development, whereby the herbicide inhibits the growth of the plant or kills the plant.

Interaction: quality or state of mutual action such that the effectiveness or toxicity of one protein or compound on another protein is inhibitory (antagonists) or enhancing (agonists).

A nucleic acid sequence is "isocoding with" a reference nucleic acid sequence when the nucleic acid sequence encodes a polypeptide having the same amino acid sequence as the polypeptide encoded by the reference nucleic acid sequence.

Isogenic: plants that are genetically identical, except that they may differ by the presence or absence of a heterologous DNA sequence.

Isolated: in the context of the present invention, an isolated DNA molecule or an isolated enzyme is a DNA molecule or enzyme that, by the hand of man, exists apart from its native environment and is therefore not a product of nature. An isolated DNA molecule or enzyme may exist in a purified form or may exist in a non-native environment such as, for example, in a transgenic host cell.

Mature protein: protein from which the transit peptide, signal peptide, and/or propeptide portions have been removed.

Minimal Promoter: the smallest piece of a promoter, such as a TATA element, that can support any transcription. A minimal promoter typically has greatly reduced promoter activity in the absence of upstream activation. In the presence of a suitable transcription factor, the minimal promoter functions to permit transcription.

Modified Enzyme Activity: enzyme activity different from that which naturally occurs in a plant (i.e. enzyme activity that occurs naturally in the absence of direct or indirect manipulation of such activity by man), which is tolerant to inhibitors that inhibit the naturally occurring enzyme activity.

Native: refers to a gene that is present in the genome of an untransformed plant cell.

Naturally occurring: the term "naturally occurring" is used to describe an object that can be found in nature as distinct from being artificially produced by man. For example, a protein or nucleotide sequence present in an organism (including a virus), which can be isolated from a source in nature and which has not been intentionally modified by man in the laboratory, is naturally occurring.

Nucleic acid: the term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19: 5081 (1991); Ohtsuka et al., *J. Biol. Chem.* 260: 2605–2608 (1985); Rossolini et al., *Mol. Cell. Probes* 8: 91–98 (1994)). The terms "nucleic acid" or "nucleic acid sequence" may also be used interchangeably with gene, cDNA, and mRNA encoded by a gene.

"ORF" means open reading frame.

Percent identity: the phrases "percent identical" or "percent identical," in the context of two nucleic acid or protein sequences, refers to two or more sequences or subsequences that have for example 60%, preferably 70%, more preferably 80%, still more preferably 90%, even more preferably 95%, and most preferably at least 99% nucleotide or amino acid residue identity, when compared and aligned for maximum correspondence, as measured using one of the following sequence comparison algorithms or by visual inspection. Preferably, the percent identity exists over a region of the sequences that is at least about 50 residues in length, more preferably over a region of at least about 100 residues, and most preferably the percent identity exists over at least about 150 residues. In an especially preferred embodiment, the percent identity exists over the entire length of the coding regions.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2: 482 (1981), by the homology alignment algorithm of Needleman & Wunsch, *J. Mol. Biol.* 48: 443 (1970), by the search for similarity method of Pearson & Lipman, *Proc. Nat'l. Acad. Sci. USA* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., *J. Mol. Biol.* 215: 403–410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. A cad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sc. USA* 90: 5873–5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Pre-protein: protein that is normally targeted to a cellular organelle, such as a chloroplast, and still comprises its native transit peptide.

Purified: the term "purified," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel. Particularly, it means that the nucleic acid or protein is at least about 50% pure, more preferably at least about 85% pure, and most preferably at least about 99% pure.

Two nucleic acids are "recombined" when sequences from each of the two nucleic acids are combined in a progeny nucleic acid. Two sequences are "directly" recombined when both of the nucleic acids are substrates for recombination. Two sequences are "indirectly recombined" when the sequences are recombined using an intermediate such as a cross-over oligonucleotide. For indirect recombination, no more than one of the sequences is an actual substrate for recombination, and in some cases, neither sequence is a substrate for recombination.

"Regulatory elements" refer to sequences involved in controlling the expression of a nucleotide sequence. Regulatory elements comprise a promoter operatively linked to the nucleotide sequence of interest and termination signals. They also typically encompass sequences required for proper translation of the nucleotide sequence.

Significant Increase: an increase in enzymatic activity that is larger than the margin of error inherent in the measurement technique, preferably an increase by about 2-fold or greater of the activity of the wild-type enzyme in the presence of the inhibitor, more preferably an increase by about 5-fold or greater, and most preferably an increase by about 10-fold or greater.

Significantly less: means that the amount of a product of an enzymatic reaction is reduced by more than the margin of error inherent in the measurement technique, preferably a decrease by about 2-fold or greater of the activity of the wild-type enzyme in the absence of the inhibitor, more preferably an decrease by about 5-fold or greater, and most preferably an decrease by about 10-fold or greater.

Specific Binding/Immunological Cross-Reactivity: An indication that two nucleic acid sequences or proteins are substantially identical is that the protein encoded by the first nucleic acid is immunologically cross reactive with, or specifically binds to, the protein encoded by the second nucleic acid. Thus, a protein is typically substantially identical to a second protein, for example, where the two proteins differ only by conservative substitutions. The phrase "specifically (or selectively) binds to an antibody," or "specifically (or selectively) immunoreactive with," when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies raised to the protein with the amino acid sequence encoded by any of the nucleic acid sequences of the invention can be selected to obtain antibodies specifically immunoreactive with that protein and not with other proteins except for polymorphic variants. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See Harlow and Lane (1988) *Antibodies, A Laboratory Manual*, Cold Spring Harbor Publications, New York ("Harlow and Lane"), for a description of immunoassay formats and conditions that can be used to determine specific immunoreactivity. Typically a specific or selective reaction will be at least twice background signal or noise and more typically more than 10 to 100 times background.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) *Laboratory Techniques in Biochemistry and Molecular Biology-Hybridization with Nucleic Acid Probes* part I chapter 2 "Overview of principles of hybridization and the strategy of nucleic acid probe assays" Elsevier, N.Y. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2×(or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone nucleotide sequences that are homologues of reference nucleotide sequences of the present invention: a reference nucleotide sequence preferably hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.

A "subsequence" refers to a sequence of nucleic acids or amino acids that comprise a part of a longer sequence of nucleic acids or amino acids (e.g., protein) respectively.

Substrate: a substrate is the molecule that an enzyme naturally recognizes and converts to a product in the biochemical pathway in which the enzyme naturally carries out its function, or is a modified version of the molecule, which is also recognized by the enzyme and is converted by the enzyme to a product in an enzymatic reaction similar to the naturally-occurring reaction.

Transformation: a process for introducing heterologous DNA into a plant cell, plant tissue, or plant. Transformed plant cells, plant tissue, or plants are understood to encompass not only the end product of a transformation process, but also transgenic progeny thereof.

"Transformed," "transgenic," and "recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed," "non-transgenic," or "non-recombinant" host refers to a wild-type organism, e.g., a bacterium or plant, which does not contain the heterologous nucleic acid molecule.

Viability: "viability" as used herein refers to a fitness parameter of a plant. Plants are assayed for their homozygous performance of plant development, indicating which proteins are essential for plant growth.

DETAILED DESCRIPTION OF THE INVENTION

I. A. General Description of Trait Functional Genomics Project

The goal of functional genomics is to assign functions to the genes of an organism using a variety of methodologies, including but not limited to bioinformatics, gene expression studies, gene and gene product interactions, genetics, biochemistry and molecular genetics. For example, bioinformatics can assign function to a given gene by identifying genes in heterologous organisms with a high degree of similarity (homology) at the amino acid or nucleotide level. Expression of a gene at the mRNA or protein levels can assign function by linking expression of a gene to an environmental response, a developmental process or a genetic (mutational) or molecular genetic (gene overexpression or underexpression) perturbation. Expression of a gene at the mRNA level can be ascertained either alone (Northern analysis) or in concert with other genes (microarray analysis), whereas expression of a gene at the protein level can be ascertained either alone (native or denatured protein gel or immunoblot analysis) or in concert with other genes (proteomic analysis). Knowledge of protein/protein and protein/DNA interactions can assign function by identifying proteins and nucleic acid sequences acting together in the same biological process. Genetics can assign function to a gene by demonstrating that DNA lesions (mutations) in the gene have a quantifiable effect on the organism, including but not limited to: its development; hormone biosynthesis and response; growth and growth habit (plant architecture);

mRNA expression profiles; protein expression profiles; ability to resist diseases; tolerance of abiotic stresses; ability to acquire nutrients; photosynthetic efficiency; altered primary and secondary metabolism; and the composition of various plant organs. Biochemistry can assign function by demonstrating that the protein encoded by the gene, typically when expressed in a heterologous organism, possesses a certain enzymatic activity, alone or in combination with other proteins. Molecular genetics can assign function by overexpressing or underexpressing the gene in the native plant or in heterologous organisms, and observing quantifiable effects as described in functional assignment by genetics above.

It is recognized by those skilled in the art that these different methodologies can each provide data as evidence for the function of a particular gene, and that such evidence is stronger with increasing amounts of data used for functional assignment: preferably from a single methodology, more preferably from two methodologies, and even more preferably from more than two methodologies. In addition, those skilled in the art are aware that different methodologies can differ in the strength of the evidence for the assignment of gene function. Typically, but not always, a datum of biochemical, genetic and molecular genetic evidence is considered stronger than a datum of bioinformatic or gene expression evidence. Finally, those skilled in the art recognize that, for different genes, a single datum from a single methodology can differ in terms of the strength of the evidence provided by each distinct datum for the assignment of the function of these different genes.

The objective of trait functional genomics is to identify crop trait genes, i.e. genes capable of conferring useful agronomic traits in crop plants. Such agronomic traits include, but are not limited to: enhanced yield, whether in quantity or quality; enhanced nutrient acquisition and enhanced metabolic efficiency; enhanced or altered nutrient composition of plant tissues used for food, feed, fiber or processing; enhanced resistance to plant diseases; enhanced tolerance of adverse environmental conditions (abiotic stresses) including but not limited to drought, excessive cold, excessive heat, or excessive soil salinity or extreme acidity or alkalinity; and alterations in plant architecture or development, including changes in developmental timing. The deployment of such identified trait genes could materially improve crop plants for the benefit of agriculture, potentially, irrespective of the method of deployment of such genes.

Cereals are the most important crop plants on the planet, in terms of both human and animal consumption. Genomic synteny (conservation of gene order within large chromosomal segments) is observed in the rice, maize, wheat, barley, rye, oats and other agriculturally important monocots, which facilitates the mapping and isolation of orthologous genes from diverse cereal species based on the sequence of a single cereal gene. Rice has the smallest (~430 Mb) genome among the cereal grains, and has recently been a major focus of public and private genomic and EST sequencing efforts.

To identify crop trait genes in the rice genome, genes with likely or demonstrated effects on agronomic traits of interest as defined above were identified in the scientific literature. The predicted peptides encoded by these genes were then used to search a proprietary database of rice genomic sequences for those with high similarity, using search algorithms familiar to those skilled in the art, resulting in the identification of rice trait gene orthologs. Rice trait gene orthologs were assigned function based on similarity searches of two different public databases: the SwissProt protein database and the GenPept non-redundant (nr) database of conceptual translations of all of the nucleotide sequences in Genbank.

To demonstrate the validity of this approach, and to provide additional evidence for the function of a subset of these genes, full-length and partial cDNAs of rice trait gene orthologs were isolated. Several different commercially available gene prediction programs were used to help predict full-length cDNAs corresponding to the putative rice trait gene orthologs. Full-length and partial cDNAs were isolated based on these predictions, using two different approaches. In one approach, a similarity search algorithm was used to search a database of sequenced cDNA clones. In another approach, the predicted cDNAs were used in combination with the genomic sequence to design primers for PCR amplification using a commercially available PCR primer-picking program. Primers were used for PCR amplification of full-length or partial cDNAs from rice cDNA libraries or first-strand cDNA. cDNA clones resulting from either approach were used for the construction of vectors designed for overexpression or underexpression of corresponding genes in transgenic rice plants. Assays to identify transgenic plants for alterations in traits of interest are to be used to unambiguously assign the utility of these genes for the improvement of rice, and by extension, other cereals, either by transgenic or classical breeding methods.

II. Identifying, Cloning and Sequencing cDNAs

The identification of genes of interest and determination of cDNA homologies is set forth in Example 1. The cloning and sequencing of the cDNAs of the present invention are described in Example 2.

The isolated nucleic acids and proteins of the present invention are usable over a range of plants, monocots and dicots, in particular monocots such as rice, wheat, barley and maize. In a more preferred embodiment, the monocot is a cereal. In a more preferred embodiment, the cereal may be, for example, maize, wheat, barley, oats, rye, millet, sorghum, triticale, secale, einkorn, spelt, emmer, teff, milo, flax, gramma grass, *Tripsacum* sp., or teosinte. In a most preferred embodiment, the cereal is rice. Other plants genera include, but are not limited to, *Cucurbita, Rosa, Vitis, Juglans, Gragaria, Lotus, Medicago, Onobrychis, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium*, and *Triticum*.

The present invention provides isolated nucleic acid molecules of RNA, DNA and analogs and/or chimeras thereof, comprising a polynucleotide of the present invention.

An isolated nucleic acid molecule of the present invention is includes:

a) an isolated nucleic acid molecule encoding an amino acid sequence of SEQ ID NO:2, and conservatively modified and polymorphic variants thereof, b) an isolated nucleic acid molecule of SEQ ID NO:1;

c) an isolated nucleic acid molecule which selectively hybridizes to a nucleic acid molecule of (a) or (b);

d) complementary sequence of nucleic acid molecules of (a,) (b), or (c); and e) an isolated nucleic acid molecule which is the reverse complement of (a), (b) or (c).

Embodiments of the present invention also relate to the an isolated nucleic acid molecule comprising or consisting of a nucleotide sequence, its complement, or its reverse complement, encoding a polypeptide including:

(a) a polypeptide sequence listed in SEQ ID NO:2, or a fragment, domain, repeat, feature, or chimera thereof;

(b) a polypeptide sequence having substantial similarity to (a);

(c) a polypeptide sequence encoded by a nucleotide sequence identical to or having substantial similarity to a nucleotide sequence listed in SEQ ID NO:1, or a fragment, domain, or feature thereof, or a sequence complementary thereto;

(d) a polypeptide sequence encoded by a nucleotide sequence capable of hybridizing under high stringency conditions to a nucleotide sequence listed in SEQ ID NO:1, or to a sequence complementary thereto; and (e) a functional fragment of (a), (b), (c) or (d).

The present invention provides methods for sequence shuffling using nucleic acid molecules of the present invention, and composition produced therefrom. DNA shuffling is a method to introduce mutations or rearrangements, preferably randomly, in a DNA molecule or a method to generate exchanges of DNA sequences between two or more DNA molecules, preferably randomly. The DNA molecule resulting from DNA shuffling is a "shuffled DNA molecule," that is a non-naturally occurring DNA molecule derived from at least one template DNA molecule. The shuffled DNA encodes an enzyme or protein modified with respect to that encoded by the template DNA, and preferably has an altered biological activity with respect to that ncoded by the template DNA. Gene shuffling is described, for example, in Stemmer et al., *PNAS* 91: 10747–10751 (1994); PCT publication No. WO 96/19256 or Zhang et al. PNAS USA 94:4504–09 (1997).

Embodiments of the present invention also relate to a shuffled nucleic acid containing a plurality of nucleotide sequence fragments, wherein at least one of the fragments corresponds to a region of a nucleotide sequence listed in SEQ ID NO:1, and wherein at least two of the plurality of sequence fragments are in an order, from 5' to 3' which is not an order in which the plurality of fragments naturally occur in a nucleic acid. In a more preferred embodiment, all of the fragments in a shuffled nucleic acid containing a plurality of nucleotide sequence fragments are from a single gene. In a more preferred embodiment, the plurality of fragments originates from at least two different genes. In a more preferred embodiment, the shuffled nucleic acid is operably linked to a promoter sequence. Another more preferred embodiment is a chimeric polynucleotide including a promoter sequence operably linked to the shuffled nucleic acid. In a more preferred embodiment, the shuffled nucleic acid is contained within a host cell.

Embodiments of the present invention contemplate a polypeptide containing a polypeptide sequence encoded by an isolated nucleic acid which includes a shuffled nucleic acid containing a plurality of nucleotide sequence fragments, wherein at least one of the fragments corresponds to a region of a nucleotide sequence listed in SEQ ID NO:1, and wherein at least two of the plurality of sequence fragments are in an order, from 5' to 3' which is not an order in which the plurality of fragments naturally occur in a nucleic acid, or functional fragment thereof.

Embodiments of the present invention further relate to an isolated polynucleotide including a nucleotide sequence of at least 10 bases, which sequence is identical, complementary, or substantially similar to a region of any sequence of SEQ ID NO:1, and wherein the polynucleotide is adapted for any of numerous uses.

Embodiments of the present invention contemplate a polypeptide containing a polypeptide sequence encoded by an isolated polynucleotide containing a nucleotide sequence of at least 10 bases, which sequence is identical, complementary, or substantially similar to a region of any of sequences of SEQ ID NO:1, and wherein the polynucleotide is adapted for a use including:

(a) use as a chromosomal marker to identify the location of the corresponding or complementary polynucleotide on a native or artificial chromosome;

(b) use as a marker for RFLP analysis;

(c) use as a marker for quantitative trait linked breeding;

(d) use as a marker for marker-assisted breeding;

(e) use as a bait sequence in a two-hybrid system to identify sequence encoding polypeptides interacting with the polypeptide encoded by the bait sequence;

(f) use as a diagnostic indicator for genotyping or identifying an individual or population of individuals; and (g) use for genetic analysis to identify boundaries of genes or exons;

(h) or functional fragment thereof.

In a preferred embodiment, the substantial similarity is at least about 80% identity, preferably 90%, more preferably at least about 95%, and most preferably at least about 99% identity to the nucleotide sequence listed in SEQ ID NO:1, fragment, domain, or feature thereof.

In a preferred embodiment, the sequence having substantial similarity to the nucleotide sequence listed in SEQ ID NO:1, fragment, domain, or feature thereof, is from a plant. In a preferred embodiment, the plant is a dicot. In another preferred embodiment, the plant is a gymnosperm. In a more preferred embodiment, the plant is a monocot. In a more preferred embodiment, the monocot is a cereal. In a more preferred embodiment, the cereal may be, for example, maize, wheat, barley, oats, rye, millet, sorghum, triticale, secale, einkorn, spelt, emmer, teff, milo, flax, gramma grass, *Tripsacum* sp., or teosinte. In a most preferred embodiment, the cereal is rice.

In a preferred embodiment, the nucleic acid molecule is expressed in a plant, preferably, throughout the plant.

In a preferred embodiment, the nucleic acid is expressed in a specific location or tissue of a plant. In a more preferred embodiment, the location or tissue is for example, but not limited to, epidermis, vascular tissue, meristem, cambium, cortex or pith. In a most preferred embodiment, the location or tissue is leaf or sheath, root, flower, developing ovule and seed. In another preferred embodiment, the nucleic acid encodes a polypeptide involved in resistance to a disease or pathogen. Preferably, the disease is a virus, viroid, bacteria or fungus. The pathogen is also preferably a nematode or insect.

In a preferred embodiment, the isolated nucleic acid comprising or consisting of a nucleotide sequence capable of hybridizing to a nucleotide sequence listed in SEQ ID NO:1, or fragment, domain, or feature thereof, and wherein the nucleic acid encodes a polypeptide involved in disease resistance. In a preferred embodiment, hybridization allows the sequence to form a duplex at high stringency conditions. Embodiments of the present invention also encompass a nucleotide sequence complementary to a nucleotide sequence listed in SEQ ID NO:1, or fragment, domain, or feature thereof. Embodiments of the present invention further encompass a nucleotide sequence complementary to a nucleotide sequence that has substantial similarity or is capable of hybridizing to a nucleotide sequence listed in SEQ ID NO:1, or fragment, domain, or feature thereof.

In a preferred embodiment, the nucleotide sequence having substantial similarity is an allelic variant of the nucleotide sequence listed in SEQ ID NO:1, or fragment, domain, or feature thereof. In an alternate embodiment, the sequence having substantial similarity is a naturally occurring variant. In another alternate embodiment, the sequence having SEQ ID NO:1, or fragment, domain, or feature thereof.

In a preferred embodiment, the isolated nucleic acid contains a plurality of regions having the nucleotide sequence listed in SEQ ID NO:1, or exon, domain, or feature thereof.

In a preferred embodiment, the sequence of the isolated nucleic acid encodes a polypeptide useful for generating an antibody having immunoreactivity against a polypeptide encoded by a nucleotide sequence listed in SEQ ID NO:2, or fragment, domain, or feature thereof.

In a preferred embodiment, the sequence having substantial similarity contains a deletion or insertion of at least one nucleotide. In a more preferred embodiment, the deletion or insertion is of less than about thirty nucleotides. In a most preferred embodiment, the deletion or insertion is of less than about five nucleotides.

In a preferred embodiment, the sequence of the isolated nucleic acid having substantial similarity comprises or consists of a substitution in at least one codon. In a preferred embodiment, the substitution is conservative.

In a preferred embodiment, the polynucleotide is used as a chromosomal marker. In another preferred embodiment, the polynucleotide is used as a marker for RFLP analysis. In another preferred embodiment, the polynucleotide is used as a marker for quantitative trait linked breeding. In another preferred embodiment, the polynucleotide is used as a marker for marker-assisted breeding. In another preferred embodiment, the polynucleotide is used as a bait sequence in a two-hybrid system to identify sequence-encoding polypeptides interacting with the polypeptide encoded by the bait sequence. In another preferred embodiment, the polynucleotide is used as a diagnostic indicator for genotyping or identifying an individual or population of individuals. In another preferred embodiment, the polynucleotide is used for genetic analysis to identify boundaries of genes or exons.

The present invention also provides a method of genotyping a plant or plant part comprising a nucleic acid molecule of the present invention. Optionally, the plant is a monocot such as, but not limited rice or wheat. Genotyping provides a means of distinguishing homologs of a chromosome pari and can be used to differentiate segregants in a plant population. Molecular marker methods can be used in phylogenetic studies, characterizing genetic relationships among crop varieties, identifying crosses or somatic hybrids, localizing chromosomeal segments affecting mongenic traits, map based cloning, and the study of quantitative inheritance (see *Plant Molecular Biology: A Laboratory Manual*, Chapter 7, Clark ed., Springer-Verlag, Berlin 1997; Paterson, A. H., "The DNA Revolution", chapter 2 in *Genome Mapping in Plants*, Paterson, A. H. ed., Academic Press/R. G. Lands Co., Austin, Tex. 1996).

The method of genotyping may employ any number of molecular marker analytical techniques such as, but not limited to, restriction length polymorphisms (RFLPs). As is well known in the art, RFLPs are produced by differences in the DNA restriction fragment lengths resulting from nucleotide differences between alleles of the same gene. Thus, the present invention provides a method of following segregation of a gene or nucleic acid of the present invention or chromosomal sequences genetically linked by using RFLP analysis. Linked chromosomal sequences are within 50 centiMorgans (50 cM), within 40 or 30 cM, preferably within 20 or 10 cM, more preferably within 5, 3, 2, or 1 cM of the nucleic acid of the invention.

III. Traits of Interest

The present invention encompasses the identification and isolation of cDNAs encoding the RAR1 rice homolog which functions in disease resistance. Additionally, altering or increasing the expression of the RAR1 gene is used to improve or modify the rice plants to be more resistant to diseases. Alternatively, decreasing the expression of the RAR1 gene is used to make plants more susceptible to diseases for use in, for example, studying disease resistance and disease modes of action. Examples below describe the isolated gene of interest and methods of analyzing the alteration of expression and their effects on the plant characteristics.

The present invention provides compositions and methods for altering (i.e. increasing or decreasing) the level of nucleic acid molecules and polypeptides of the present invention in plants. In particular, the nucleic acid molecules and polypeptides of the invention are expressed constitutively, temporally or spatially, e.g. at developmental stages, in certain tissues, and/or quantities, which are uncharacteristic of non-recombinantly engineered plants. Therefore, the present invention provides utility in such exemplary applications as altering disease resistance in plants, altering the expression of R genes in a plant, and altering or regulating the expression of a coding sequence of interest in a plant.

Pathogens of the invention include, but are not limited to, fungi, bacteria, nematodes, viruses or viroids, etc.

Generally Viruses include tobacco or cucumber mosaic virus, ringspot virus, necrosis virus, maize dwarf mosaic virus, etc. Specific fungal, bacterial and viral pathogens of major crops include, but are not limited to: RICE: rice brown spot fungus (*Cochliobolus miyabeanus*), rice blast fungus—*Magnaporthe grisea* (*Pyricularia grisea*), *Magnaporthe salvinii* (*Sclerotium oryzae*), *Xanthomomas oryzae* pv. *oryzae*, *Xanthomomas oryzae* pv. *oryzicola*, *Rhizoctonia* spp. (including but not limited to *Rhizoctonia solani*, *Rhizoctonia oryzae* and *Rhizoctonia oryzae-sativae*), *Pseudomonas* spp. (including but not limited to *Pseudomonas plantarii*, *Pseudomonas avenae*, *Pseudomonas glumae*, *Pseudomonas fuscovaginae*, *Pseudomonas alboprecipitans*, *Pseudomonas syringae* pv. *panici*, *Pseudomonas syringae* pv. *syringae*, *Pseudomonas syringae* pv. *oryzae* and *Pseudomonas syringae* pv. *aptata*), *Erwinia* spp. (including but not limited to *Erwinia herbicola*, *Erwinia amylovaora*, *Erwinia chrysanthemi* and *Erwinia carotovora*), *Achyla* spp. (including but not limited to *Achyla conspicua* and *Achyla klebsiana*), *Pythium* spp. (including but not limited to *Pythium dissotocum*, *Pythium irregulare*, *Pythium arrhenomanes*, *Pythium myriotylum*, *Pythium catenulatum*, *Pythium graminicola* and *Pythium spinosum*), *Saprolegnia* spp., *Dictyuchus* spp., *Pythiogeton* spp., *Phytophthora* spp., *Alternaria padwickii*, *Cochliobolus miyabeanus*, *Curvularia* spp. (including but not limited to *Curvularia lunata*, *Curvularia affinis*, *Curvularia clavata*, *Curvularia eragrostidis*, *Curvularia fallax*, *Curvularia geniculata*, *Curvularia inaequalis*, *Curvularia intermedia*, *Curvularia oryzae*, *Curvularia oryzae-sativae*, *Curvularia pallescens*, *Curvularia senegalensis*, *Curvularia tuberculate*, *Curvularia uncinata* and *Curvularia verrucu-* losa), *Sarocladium oryzae, Gerlachia oryzae, Fusarium* spp. (including but not limited *Fusarium graminearum, Fusarium nivale* and to different pathovars of *Fusarium monoliforme,* including pvs. *fujikuroi* and *zeae*), *Sclerotium rolfsii, Phoma exigua, Mucor fragilis, Trichoderma viride, Rhizopus* spp., *Cercospora oryzae, Entyloma oryzae, Dreschlera gigantean, Sclerophthora macrospora, Mycovellosiella oryzae, Phomopsis oryzae-sativae, Puccinia graminis, Uromyces coronatus, Cylindrocladium scoparium, Sarocladium oryzae, Gaeumannomyces graminis* pv. *graminis, Myrothecium verrucaria, Pyrenochaeta oryzae, Ustilaginoidea virens, Neovossia* spp. (including but not limited to Neovossia horrida), *Tilletia* spp., *Balansia oryzae-sativae, Phoma* spp. (including but not limited to *Phoma sorghina, Phoma insidiosa, Phoma glumarum, Phoma glumicola* and *Phoma oryzina*), *Nigrospora* spp. (including but not limited to *Nigrospora oryzae, Nigrospora sphaerica, Nigrospora panici* and *Nigrospora padwickii*), *Epiococcum nigrum, Phyllostica* spp., *Wolkia decolorans, Monascus purpureus, Aspergillus* spp., *Penicillium* spp., *Absidia* spp., *Mucor* spp., *Chaetomium* spp., *Dematium* spp., *Monilia* spp., *Streptomyces* spp., *Syncephalastrum* spp., *Verticillium* spp., *Nematospora coryli, Nakataea sigmoidea, Cladosporium* spp., *Bipolaris* spp., *Coniothyrium* spp., *Diplodia oryzae, Exserophilum rostratum, Helococera oryzae, Melanomma glumarum, Metashaeria* spp., *Mycosphaerella* spp., *Oidium* spp., *Pestalotia* spp., *Phaeoseptoria* spp., *Sphaeropsis* spp., *Trematosphaerella* spp., rice black-streaked dwarf virus, rice dwarf virus, rice gall dwarf virus, barley yellow dwarf virus, rice grassy stunt virus, rice hoja blanca virus, rice necrosis mosaic virus, rice ragged stunt virus, rice stripe virus, rice stripe necrosis virus, rice transitory yellowing virus, rice tungro bacilliform virus, rice tungro spherical virus, rice yellow mottle virus, rice tarsonemid mite virus, Echinochloa hoja blanca virus, Echinochloa ragged stunt virus, orange leaf mycoplasma-like organism, yellow dwarf mycoplasma-like organism, *Aphelenchoides besseyi, Ditylenchus angustus, Hirschmanniella* spp., *Criconemella* spp., *Meloidogyne* spp., *Heterodera* spp., *Pratylenchus* spp., *Hoplolaimus indicus:*

SOYBEANS: *Phytophthora sojae, Fusarium solani* f. sp. Glycines, *Macrophomina phaseolina, Fusarium, Pythium, Rhizoctonia, Phialophora gregata, Sclerotinia sclerotiorum, Diaporthe phaseolorum* var. *sojae, Colletotrichum truncatum, Phomopsis longicolla, Cercosporakikuchii, Diaporthe phaseolorum* var. *meridionalis* (and var. *caulivora), Phakopsora pachyrhyzi, Fusarium solani, Microsphaera diffusa, Septoria* glycines, *Cercospora kikuchii, Macrophomina phaseolina, Sclerotinia sclerotiorum, Corynespora cassiicola, Rhizoctonia solani, Cercospora sojina, Phytophthora megasperma* fsp. *glycinea, Macrophomina phaseolina, Fusarium oxysporum, Diapothe phaseolorum* var. *sojae (Phomopsis sojae), Diaporthe phaseolorum* var. *caulivora, Sclerotium rolfsii, Cercospora kikuchii, Cercospora sojina, Peronospora manshurica, Colletotrichum dematium (Colletotichum truncatum), Corynespora cassiicola, Phyllosticta sojicola, Alternaria alternata, Pseudomonas syringae* p.v. *glycinea, Xanthomonas campestris* p.v. *phaseoli, Microspaera diffusa, Fusarium semitectum, Phialophora gregata,* Soybean mosaic virus, *Glomerella* glycines, Tobacco Ring spot virus, Tobacco Streak virus, *Phakopsora pachyrhyzi, Pythium aphanidermatum, Pythium ultimum, Pythium dearyanum,* Tomato spotted wilted virus, *Heterodera* glycines, *Fusarium solani,* Soybean cyst and root knot nematodes.

CORN: *Fusarium moniliforme* var. *subglutinans, Erwinia stewartii, Fusarium moniliforme, Gibberella zeae (Fusarium Graminearum), Stenocarpella maydi (Diplodia maydis), Pythium irregulare, Pythium debaryanum, Pythium graminicola, Pythium splendens, Pythium ultimum, Pythium aphanidermatum, Aspergillus flavus, Bipolaris maydis* O, T (*cochliobolus heterostrophus*), *Helminthosporium carbonum* I, II, and III (*Cochliobolus* carbonum), *Exserohilum turcicum* I, II and III, *Helminthosporium pedicellatum, Physoderma maydis, Phyllosticta maydis, Kabatie-maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganese* subsp. *Nebraskense, Trichoderma viride,* Maize dwarf Mosaic Virus A and B, Wheat Streak Mosaic Virus, Maize Chlorotic Dwarf Virus, *Claviceps sorghi, Pseudonomas avenae, Erwinia chrysantemi* p.v. *Zea, Erwinia corotovora, Cornstun spiroplasma, Diplodia macrospora, Sclerophthora macrospora, Peronosclerospora sorghi, Peronoscherospora philippinesis, Peronosclerospora maydis, Peronosclerospora sacchari, Spacelotheca reiliana, Physopella zea, Cephalosporium maydis, Caphalosporium acremonium,* Maize Chlorotic Mottle Virus, High Plains Virus, Maize Mosaic Virus, Maize Rayado Fino Virus, Maize Streak Virus, Maize Stripe Virus, Maize Rought Dwarf Virus:

WHEAT: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f. sp. *Tritici, Puccinia graminis* f. sp. *Tritici, Puccinia recondite* f. sp. *tritici, puccinia striformis, Pyrenophora triticirepentis, Septoria nodorum, Septoria tritici, Spetoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana,* Barley Yellow Dwarf Virus, Brome Mosaic Virus, Soil Borne Wheat Mosaic Virus, Wheat Streak Virus, Wheat Spindle Streak Virus, American Wheat Striate Virus, *Claviceps purpurea, Tilletia tritici, Tilletia laevis, Pstilago tritici, Tilletia indica, Rhizoctonia solani, Pythium arrhenomannes, Pythium gramicola, Pythium aphanidermatum,* High Plains Virus, European Wheat Striate Virus:

CANOLA: *Albugo candida, Alternaria brassicae, Leptosharia maculans, Rhizoctonia solani, Sclerotinia sclerotiorum, Mycospaerella brassiccola, Pythium ultimum, Peronospora parasitica, Fusarium roseum, Alternaria alternata:*

SUNFLOWER: *Plasmophora halstedii, Scherotinia sclerotiorum,* Aster Yellows, *Septoria helianthi, Phomopsis helianthi, Alternaria helianthi, Alternaria zinniae, Botrytis cinera, Phoma macdonaldii, Macrophomina phaseolina, Erysiphe cichoracearum, Phizopus oryzae, Rhizopus arrhizus, Rhizopus stolonifer, Puccinia helianthi, Verticillium Dahliae, Erwinia carotovorum* p.v. *carotovora, Cephalosporium acremonium, Phytophthora cryptogea, Albugo tragopogonis*: etc.

SORGHUM: *Exserohilum turcicum, Colletotrichum graminicola (Glomerella graminicola), Cercospora sorghi, Gloeocercospora sorghi, Ascochyta sorghi, Pseudomonas syringae* p.v. *syringae, Xanthomonas campestris* p.v. *holcicola, Pseudomonas andropogonis, Puccinia purpurea, Macrophomina phaseolina, Periconia circinata, Fusarium moniliforme, Alternaria alternate, Bipolaris sorghicola,*

*Helminthosporium sorghicola, Curvularia lunata, Phoma insidiosa, Pseudomonas avenae* (*Pseudomonas alboprecipitans*), *Ramulispora sorghi, Ramulispora sorghicola, Phyllachara sacchari, Sporisorium relianum* (*Sphacelotheca reliana*), *Sphacelotheca cruenta, Sporisorium sorghi,* Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium Oxysporum, Pythium arrhenomanes, Pythium graminicola,* etc.

ALFALFA: *Clavibater michiganensis* subsp. *Insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium oxysporum, Rhizoctonia solani, Uromycesstriatus, Colletotrichum trifolii* race 1 and race 2, *Leptosphaerulina briosiana, Stemphylium botryosum, Stagonospora meliloti, Sclerotinia trifoliorum,* Alfalfa Mosaic Virus, *Verticillium alboatrum, Xanthomonas campestris* p. v. *alfalfae, Aphanomyces euteiches, Stemphylium herbarum, Stemphylium alfalfae.*

IV. Controlling Gene Expression in Transgenic Plants

The invention further relates to transformed cells comprising the nucleic acid molecules, transformed plants, seeds, and plant parts, and methods of modifying the disease resistance characteristics of the plant by altering the expression of the genes of the invention. The invention also relates to transformed cells comprising the nucleic acid molecules of the invention and further comprising a nucleic acid molecule comprising a promoter regulated by the RAR1 gene product or polypeptide and a nucleic acid molecule encoding a coding sequence of interest, transformed plants, seeds, and plant parts, and methods of modifying the disease resistance and the expression of the gene product of interest.

A. Modification of Coding Sequences and Adjacent Sequences

The transgenic expression in plants of genes derived from heterologous sources may involve the modification of those genes to achieve and optimize their expression in plants. In particular, bacterial ORFs which encode separate enzymes but which are encoded by the same transcript in the native microbe are best expressed in plants on separate transcripts. To achieve this, each microbial ORF is isolated individually and cloned within a cassette which provides a plant promoter sequence at the 5' end of the ORF and a plant transcriptional terminator at the 3' end of the ORF. The isolated ORF sequence preferably includes the initiating ATG codon and the terminating STOP codon but may include additional sequence beyond the initiating ATG and the STOP codon. In addition, the ORF may be truncated, but still retain the required activity; for particularly long ORFs, truncated versions which retain activity may be preferable for expression in transgenic organisms. By "plant promoter" and "plant transcriptional terminator" it is intended to mean promoters and transcriptional terminators which operate within plant cells. This includes promoters and transcription terminators which may be derived from non-plant sources such as viruses (an example is the Cauliflower Mosaic Virus).

In some cases, modification to the ORF coding sequences and adjacent sequence is not required. It is sufficient to isolate a fragment containing the ORF of interest and to insert it downstream of a plant promoter. For example, Gaffney et al. (*Science* 261: 754–756 (1993)) have expressed the *Pseudomonas* nahG gene in transgenic plants under the control of the CaMV 35S promoter and the CaMV tml terminator successfully without modification of the coding sequence and with nucleotides of the *Pseudomonas* gene upstream of the ATG still attached, and nucleotides downstream of the STOP codon still attached to the nahG ORF. Preferably as little adjacent microbial sequence should be left attached upstream of the ATG and downstream of the STOP codon. In practice, such construction may depend on the availability of restriction sites.

In other cases, the expression of genes derived from microbial sources may provide problems in expression. These problems have been well characterized in the art and are particularly common with genes derived from certain sources such as *Bacillus*. These problems may apply to the nucleotide sequence of this invention and the modification of these genes can be undertaken using techniques now well known in the art. The following problems may be encountered:

1. Codon Usage.

The preferred codon usage in plants differs from the preferred codon usage in certain microorganisms. Comparison of the usage of codons within a cloned microbial ORF to usage in plant genes (and in particular genes from the target plant) will enable an identification of the codons within the ORF which should preferably be changed. Typically plant evolution has tended towards a strong preference of the nucleotides C and G in the third base position of monocotyledons, whereas dicotyledons often use the nucleotides A or T at this position. By modifying a gene to incorporate preferred codon usage for a particular target transgenic species, many of the problems described below for GC/AT content and illegitimate splicing will be overcome.

2. GC/AT Content.

Plant genes typically have a GC content of more than 35%. ORF sequences which are rich in A and T nucleotides can cause several problems in plants. Firstly, motifs of ATTTA are believed to cause destabilization of messages and are found at the 3' end of many short-lived mRNAs. Secondly, the occurrence of polyadenylation signals such as AATAAA at inappropriate positions within the message is believed to cause premature truncation of transcription. In addition, monocotyledons may recognize AT-rich sequences as splice sites (see below).

3. Sequences Adjacent to the Initiating Methionine.

Plants differ from microorganisms in that their messages do not possess a defined ribosome binding site. Rather, it is believed that ribosomes attach to the 5' end of the message and scan for the first available ATG at which to start translation. Nevertheless, it is believed that there is a preference for certain nucleotides adjacent to the ATG and that expression of microbial genes can be enhanced by the inclusion of a eukaryotic consensus translation initiator at the ATG. Clontech (1993/1994 catalog, page 210, incorporated herein by reference) have suggested one sequence as a consensus translation initiator for the expression of the *E. coli* uidA gene in plants. Further, Joshi (*N.A.R.* 15: 6643–6653 (1987), incorporated herein by reference) has compared many plant sequences adjacent to the ATG and suggests another consensus sequence. In situations where difficulties are encountered in the expression of microbial ORFs in plants, inclusion of one of these sequences at the initiating ATG may improve translation. In such cases the last three nucleotides of the consensus may not be appropriate for inclusion in the modified sequence due to their modification of the second AA residue. Preferred sequences adjacent to the initiating methionine may differ between different plant species. A survey of 14 maize genes located in the GenBank database provided the following results:

| Position Before the Initiating ATG in 14 Maize Genes: | | | | | | | | | | |
|---|---|---|---|---|---|---|---|---|---|---|
| | −10 | −9 | −8 | −7 | −6 | −5 | −4 | −3 | −2 | −1 |
| C | 3 | 8 | 4 | 6 | 2 | 5 | 6 | 0 | 10 | 7 |
| T | 3 | 0 | 3 | 4 | 3 | 2 | 1 | 1 | 1 | 0 |
| A | 2 | 3 | 1 | 4 | 3 | 2 | 3 | 7 | 2 | 3 |
| G | 6 | 3 | 6 | 0 | 6 | 5 | 4 | 6 | 1 | 5 |

This analysis can be done for the desired plant species into which the nucleotide sequence is being incorporated, and the sequence adjacent to the ATG modified to incorporate the preferred nucleotides.

4. Removal of Illegitimate Splice Sites.

Genes cloned from non-plant sources and not optimized for expression in plants may also contain motifs which may be recognized in plants as 5' or 3' splice sites, and be cleaved, thus generating truncated or deleted messages. These sites can be removed using the techniques well known in the art.

Techniques for the modification of coding sequences and adjacent sequences are well known in the art. In cases where the initial expression of a microbial ORF is low and it is deemed appropriate to make alterations to the sequence as described above, then the construction of synthetic genes can be accomplished according to methods well known in the art. These are, for example, described in the published patent disclosures EP 0 385 962 (to Monsanto), EP 0 359 472 (to Lubrizol) and WO 93/07278 (to Ciba-Geigy), all of which are incorporated herein by reference. In most cases it is preferable to assay the expression of gene constructions using transient assay protocols (which are well known in the art) prior to their transfer to transgenic plants.

B. Construction of Plant Expression Cassettes

Coding sequences intended for expression in transgenic plants are first assembled in expression cassettes behind a suitable promoter expressible in plants. The expression cassettes may also comprise any further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments. These expression cassettes can then be easily transferred to the plant transformation vectors described below. The following is a description of various components of typical expression cassettes.

1. Promoters

The selection of the promoter used in expression cassettes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and the selection will reflect the desired location of accumulation of the gene product. Alternatively, the selected promoter may drive expression of the gene under various inducing conditions. Promoters vary in their strength, i.e., ability to promote transcription. Depending upon the host cell system utilized, any one of a number of suitable promoters can be used, including the gene's native promoter.

The following are non-limiting examples of promoters that may be used in expression cassettes.

a. Constitutive Expression, the Ubiquitin Promoter: Ubiquitin is a gene product known to accumulate in many cell types and its promoter has been cloned from several species for use in transgenic plants (e.g. sunflower—Binet et al. Plant Science 79: 87–94 (1991); maize—Christensen et al. Plant Molec. Biol. 12: 619–632 (1989); and *Arabidopsis*—Callis et al., *J. Biol. Chem.* 265:12486–12493 (1990) and Norris et al., *Plant Mol. Biol.* 21:895–906 (1993)). The maize ubiquitin promoter has been developed in transgenic monocot systems and its sequence and vectors constructed for monocot transformation are disclosed in the patent publication EP 0 342 926 (to Lubrizol) which is herein incorporated by reference. Taylor et al. (Plant Cell Rep. 12: 491–495 (1993)) describe a vector (pAHC25) that comprises the maize ubiquitin promoter and first intron and its high activity in cell suspensions of numerous monocotyledons when introduced via microprojectile bombardment. The *Arabidopsis* ubiquitin promoter is ideal for use with the nucleotide sequences of the present invention. The ubiquitin promoter is suitable for gene expression in transgenic plants, both monocotyledons and dicotyledons. Suitable vectors are derivatives of pAHC25 or any of the transformation vectors described in this application, modified by the introduction of the appropriate ubiquitin promoter and/or intron sequences.

b. Constitutive Expression, the CaMV 35S Promoter:

Construction of the plasmid pCGN1761 is described in the published patent application EP 0 392 225 (Example 23), which is hereby incorporated by reference. pCGN1761 contains the "double" CaMV 35S promoter and the tml transcriptional terminator with a unique EcoRI site between the promoter and the terminator and has a pUC-type backbone. A derivative of pCGN1761 is constructed which has a modified polylinker which includes NotI and XhoI sites in addition to the existing EcoRI site. This derivative is designated pCGN1761ENX. pCGN1761ENX is useful for the cloning of cDNA sequences or coding sequences (including microbial ORF sequences) within its polylinker for the purpose of their expression under the control of the 35S promoter in transgenic plants. The entire 35S promoter-coding sequence-tml terminator cassette of such a construction can be excised by HindIII, SphI, SalI, and XbaI sites 5' to the promoter and XbaI, BamHI and BglII sites 3' to the terminator for transfer to transformation vectors such as those described below. Furthermore, the double 35S promoter fragment can be removed by 5' excision with HindIII, SphI, SalI, XbaI, or PstI, and 3' excision with any of the polylinker restriction sites (EcoRI, NotI or XhoI) for replacement with another promoter. If desired, modifications around the cloning sites can be made by the introduction of sequences that may enhance translation. This is particularly useful when overexpression is desired. For example, pCGN1761ENX may be modified by optimization of the translational initiation site as described in Example 37 of U.S. Pat. No. 5,639,949, incorporated herein by reference.

c. Constitutive Expression, the Actin Promoter:

Several isoforms of actin are known to be expressed in most cell types and consequently the actin promoter is a good choice for a constitutive promoter. In particular, the promoter from the rice Act1 gene has been cloned and characterized (McElroy et al. Plant Cell 2:163–171 (1990)). A 1.3 kb fragment of the promoter was found to contain all the regulatory elements required for expression in rice protoplasts. Furthermore, numerous expression vectors based on the Act1 promoter have been constructed specifically for use in monocotyledons (McElroy et al. Mol. Gen.

Genet. 231:150–160 (1991)). These incorporate the Actl-intron 1, Adhl 5' flanking sequence and Adhl-intron 1 (from the maize alcohol dehydrogenase gene) and sequence from the CaMV 35S promoter. Vectors showing highest expression were fusions of 35S and Actl intron or the Actl 5' flanking sequence and the Actl intron. Optimization of sequences around the initiating ATG (of the GUS reporter gene) also enhanced expression. The promoter expression cassettes described by McElroy et al. (Mol. Gen. Genet. 231:150–160 (1991)) can be easily modified for gene expression and are particularly suitable for use in monocotyledonous hosts. For example, promoter-containing fragments is removed from the McElroy constructions and used to replace the double 35S promoter in pCGN1761ENX, which is then available for the insertion of specific gene sequences. The fusion genes thus constructed can then be transferred to appropriate transformation vectors. In a separate report, the rice Actl promoter with its first intron has also been found to direct high expression in cultured barley cells (Chibbar et al. Plant Cell Rep. 12:506–509 (1993)).

d. Inducible Expression, PR-1 Promoters:

The double 35S promoter in pCGN1761ENX may be replaced with any other promoter of choice that will result in suitably high expression levels. By way of example, one of the chemically regulatable promoters described in U.S. Pat. No. 5,614,395, such as the tobacco PR-1a promoter, may replace the double 35S promoter. Alternately, the *Arabidopsis* PR-1 promoter described in Lebel et al., *Plant J.* 16:223–233 (1998) may be used. The promoter of choice is preferably excised from its source by restriction enzymes, but can alternatively be PCR-amplified using primers that carry appropriate terminal restriction sites. Should PCR-amplification be undertaken, then the promoter should be re-sequenced to check for amplification errors after the cloning of the amplified promoter in the target vector. The chemically/pathogen regulatable tobacco PR-1a promoter is cleaved from plasmid pCIB1004 (for construction, see example 21 of EP 0 332 104, which is hereby incorporated by reference) and transferred to plasmid pCGN1761ENX (Uknes et al., *Plant Cell* 4: 645–656(1992)). pCIB1004 is cleaved with NcoI and the resultant 3' overhang of the linearized fragment is rendered blunt by treatment with T4 DNA polymerase. The fragment is then cleaved with HindIII and the resultant PR-1a promoter-containing fragment is gel purified and cloned into pCGN1761ENX from which the double 35S promoter has been removed. This is done by cleavage with XhoI and blunting with T4 polymerase, followed by cleavage with HindIII and isolation of the larger vector-terminator containing fragment into which the pCIB1004 promoter fragment is cloned. This generates a pCGN1761ENX derivative with the PR-1a promoter and the tml terminator and an intervening polylinker with unique EcoRI and NotI sites. The selected coding sequence can be inserted into this vector, and the fusion products (i.e. promoter-gene-terminator) can subsequently be transferred to any selected transformation vector, including those described infra. Various chemical regulators may be employed to induce expression of the selected coding sequence in the plants transformed according to the present invention, including the benzothiadiazole, isonicotinic acid, and salicylic acid compounds disclosed in U.S. Pat. Nos. 5,523,311 and 5,614,395.

e. Inducible Expression, an Ethanol-Inducible Promoter:

A promoter inducible by certain alcohols or ketones, such as ethanol, may also be used to confer inducible expression of a coding sequence of the present invention. Such a promoter is for example the alcA gene promoter from *Aspergillus nidulans* (Caddick et al. (1998) *Nat. Biotechnol* 16:177–180). In *A. nidulans*, the alcA gene encodes alcohol dehydrogenase 1, the expression of which is regulated by the AlcR transcription factors in presence of the chemical inducer. For the purposes of the present invention, the CAT coding sequences in plasmid palcA:CAT comprising a alcA gene promoter sequence fused to a minimal 35S promoter (Caddick et al. (1998) *Nat. Biotechnol* 16:177–180) are replaced by a coding sequence of the present invention to form an expression cassette having the coding sequence under the control of the alcA gene promoter. This is carried out using methods well known in the art.

f. Inducible Expression, a Glucocorticoid-Inducible Promoter:

Induction of expression of a nucleic acid sequence of the present invention using systems based on steroid hormones is also contemplated. For example, a glucocorticoid-mediated induction system is used (Aoyama and Chua (1997) *The Plant Journal* 11: 605–612) and gene expression is induced by application of a glucocorticoid, for example a synthetic glucocorticoid, preferably dexamethasone, preferably at a concentration ranging from 0.1 mM to 1 mM, more preferably from 10 mM to 100 mM. For the purposes of the present invention, the luciferase gene sequences are replaced by a nucleic acid sequence of the invention to form an expression cassette having a nucleic acid sequence of the invention under the control of six copies of the GAL4 upstream activating sequences fused to the 35S minimal promoter. This is carried out using methods well known in the art. The trans-acting factor comprises the GAL4 DNA-binding domain (Keegan et al. (1986) *Science* 231: 699–704) fused to the transactivating domain of the herpes viral protein VP16 (Triezenberg et al. (1988) *Genes Devel.* 2: 718–729) fused to the hormone-binding domain of the rat glucocorticoid receptor (Picard et al. (1988) *Cell* 54: 1073–1080). The expression of the fusion protein is controlled by any promoter suitable for expression in plants known in the art or described here. This expression cassette is also comprised in the plant comprising a nucleic acid sequence of the invention fused to the 6×GAL4/minimal promoter. Thus, tissue- or organ-specificity of the fusion protein is achieved leading to inducible tissue- or organ-specificity of the insecticidal toxin.

g. Root Specific Expression:

Another pattern of gene expression is root expression. A suitable root promoter is the promoter of the maize metallothionein-like (MTL) gene described by de Framond (FEBS 290: 103–106 (1991)) and also in U.S. Pat. No. 5,466,785, incorporated herein by reference. This "MTL" promoter is transferred to a suitable vector such as pCGN1761ENX for the insertion of a selected gene and subsequent transfer of the entire promoter-gene-terminator cassette to a transformation vector of interest.

h. Wound-Inducible Promoters:

Wound-inducible promoters may also be suitable for gene expression. Numerous such promoters have been described (e.g. Xu et al. Plant Molec. Biol. 22: 573–588 (1993), Logemann et al. Plant Cell 1: 151–158 (1989), Rohrmeier & Lehle, Plant Molec. Biol. 22: 783–792 (1993), Firek et al. Plant Molec. Biol. 22: 129–142 (1993), Warner et al. Plant J. 3: 191–201 (1993)) and all are suitable for use with the instant invention. Logemann et al. describe the 5' upstream sequences of the dicotyledonous potato wunl gene. Xu et al. show that a wound-inducible promoter from the dicotyledon potato (pin2) is active in the monocotyledon rice. Further, Rohrmeier & Lehle describe the cloning of the maize Wipl cDNA which is wound induced and which can be used to isolate the cognate promoter using standard techniques. Similar, Firek et al. and Warner et al. have described a wound-induced gene from the monocotyledon *Asparagus officinalis*, which is expressed at local wound and pathogen invasion sites. Using cloning techniques well known in the art, these promoters can be transferred to suitable vectors, fused to the genes pertaining to this invention, and used to express these genes at the sites of plant wounding.

i. Pith-Preferred Expression:

Patent Application WO 93/07278, which is herein incorporated by reference, describes the isolation of the maize trpA gene, which is preferentially expressed in pith cells. The gene sequence and promoter extending up to −1726 bp from the start of transcription are presented. Using standard molecular biological techniques, this promoter, or parts thereof, can be transferred to a vector such as pCGN1761 where it can replace the 35S promoter and be used to drive the expression of a foreign gene in a pith-preferred manner. In fact, fragments containing the pith-preferred promoter or parts thereof can be transferred to any vector and modified for utility in transgenic plants.

j. Leaf-Specific Expression:

A maize gene encoding phosphoenol carboxylase (PEPC) has been described by Hudspeth & Grula (Plant Molec Biol 12: 579–589 (1989)). Using standard molecular biological techniques the promoter for this gene can be used to drive the expression of any gene in a leaf-specific manner in transgenic plants.

k. Pollen-Specific Expression:

WO 93/07278 describes the isolation of the maize calcium-dependent protein kinase (CDPK) gene which is expressed in pollen cells. The gene sequence and promoter extend up to 1400 bp from the start of transcription. Using standard molecular biological techniques, this promoter or parts thereof, can be transferred to a vector such as pCGN1761 where it can replace the 35S promoter and be used to drive the expression of a nucleic acid sequence of the invention in a pollen-specific manner.

I. RARAR1 Controlled Expression

Genes under the control of the RARAR1 protein have regulatory regions that are affected by the expression of the RARAR1 gene and resulting protein. These regulatory regions, including their promoters, can be valuable in the control of nucleic acid molecules of interest and their gene products. Such expression constructs comprising RARAR1 controlled promoters or regulatory regions and a nucleic acid molecule of interest can be transformed into cells and plants in order to affect or modify expression of the nucleic acid molecule of interest to be under the regulation of RAR1 gene product. Such nucleic acid molecule of interest could have increased or decreased expression in response to an increased or decreased expression of the RAR1 gene product.

2. Transcriptional Terminators A variety of transcriptional terminators are available for use in expression cassettes. These are responsible for the termination of transcription beyond the transgene and correct mRNA polyadenylation. Appropriate transcriptional terminators are those that are known to function in plants and include the CaMV 35S terminator, the tml terminator, the nopaline synthase (nos) terminator and the pea rbcS E9 terminator. These can be used in both monocotyledons and dicotyledons. In addition, a gene's native transcription terminator may be used.

3. Sequences for the Enhancement or Regulation of Expression

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., *Genes Develop*. 1: 1183–1200 (1987)). In the same experimental system, the intron from the maize bronze1 gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. *Nucl. Acids Res.* 15: 8693–8711 (1987); Skuzeski et al. *Plant Molec. Biol.* 15: 65–79 (1990)). Other leader sequences known in the art include but are not limited to: picornavirus leaders, for example, EMCV leader (Encephalomyocarditis 5' noncoding region) (Elroy-Stein, O., Fuerst, T. R., and Moss, B. *PNAS USA* 86:6126–6130 (1989)); potyvirus leaders, for example, TEV leader (Tobacco Etch Virus) (Allison et al., 1986); MDMV leader (Maize Dwarf Mosaic Virus); *Virology* 154:9–20); human immunoglobulin heavy-chain binding protein (BiP) leader, (Macejak, D. G., and Sarnow, P., *Nature* 353: 90–94 (1991); untranslated leader from the coat protein mRNA of alfalfa mosaic virus (AMV RNA 4), (Jobling, S. A., and Gehrke, L., *Nature* 325:622–625 (1987); tobacco mosaic virus leader (TMV), (Gallie, D. R. et al., *Molecular Biology of RNA*, pages 237–256 (1989); and Maize Chlorotic Mottle Virus leader (MCMV) (Lommel, S. A. et al., *Virology* 81:382–385 (1991). See also, Della-Cioppa et al., *Plant Physiology* 84:965–968 (1987).

In addition to incorporating one or more of the aforementioned elements into the 5' regulatory region of a target expression cassette of the invention, other elements peculiar to the target expression cassette may also be incorporated. Such elements include but are not limited to a minimal promoter. By minimal promoter it is intended that the basal promoter elements are inactive or nearly so without upstream activation. Such a promoter has low background activity in plants when there is no transactivator present or when enhancer or response element binding sites are absent. One minimal promoter that is particularly useful for target genes in plants is the Bz1 minimal promoter, which is obtained from the bronze1 gene of maize. The Bz1 core promoter is obtained from the "myc" mutant Bz1-luciferase construct pBz1LucR98 via cleavage at the NheI site located at −53 to −58. Roth et al., *Plant Cell* 3: 317 (1991). The derived Bz1 core promoter fragment thus extends from −53 to +227 and includes the Bz1 intron-1 in the 5' untranslated region. Also useful for the invention is a minimal promoter created by use of a synthetic TATA element. The TATA element allows recognition of the promoter by RNA polymerase factors and confers a basal level of gene expression in the absence of activation (see generally, Mukumoto (1993) *Plant Mol Biol* 23: 995–1003; Green (2000) *Trends Biochem Sci* 25: 59–63)

4. Targeting of the Gene Product Within the Cell

Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins which is cleaved during chloroplast import to yield the mature protein (e.g. Comai et al. J. Biol. Chem. 263: 15104–15109 (1988)). These signal sequences can be fused to heterologous gene products to effect the import of heterologous products into the chloroplast (van den Broeck, et al. Nature 313: 358–363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized. See also, the section entitled "Expression With Chloroplast Targeting" in Example 37 of U.S. Pat. No. 5,639,949.

Other gene products are localized to other organelles such as the mitochondrion and the peroxisome (e.g. Unger et al. Plant Molec. Biol. 13: 411–418 (1989)). The cDNAs encoding these products can also be manipulated to effect the targeting of heterologous gene products to these organelles. Examples of such sequences are the nuclear-encoded ATPases and specific aspartate amino transferase isoforms for mitochondria. Targeting cellular protein bodies has been described by Rogers et al. (Proc. Natl. Acad. Sci. USA 82: 6512–6516 (1985)).

In addition, sequences have been characterized which cause the targeting of gene products to other cell compartments. Amino terminal sequences are responsible for targeting to the ER, the apoplast, and extracellular secretion from aleurone cells (Koehler & Ho, Plant Cell 2: 769–783 (1990)). Additionally, amino terminal sequences in conjunction with carboxy terminal sequences are responsible for vacuolar targeting of gene products (Shinshi et al. Plant Molec. Biol. 14:357–368 (1990)).

By the fusion of the appropriate targeting sequences described above to transgene sequences of interest it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino terminal ATG of the transgene. The signal sequence selected should include the known cleavage site, and the fusion constructed should take into account any amino acids after the cleavage site which are required for cleavage. In some cases this requirement may be fulfilled by the addition of a small number of amino acids between the cleavage site and the transgene ATG or, alternatively, replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by Bartlett et al. In: Edelmann et al. (Eds.) *Methods in Chloroplast Molecular Biology*, Elsevier pp 1081–1091 (1982) and Wasmann et al. Mol. Gen. Genet. 205:446–453 (1986). These construction techniques are well known in the art and are equally applicable to mitochondria and peroxisomes.

The above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

C. Construction of Plant Transformation Vectors

Numerous transformation vectors available for plant transformation are known to those of ordinary skill in the plant transformation arts, and the nucleic acid molecules or genes pertinent to this invention can be used in conjunction with any such vectors. The selection of vector will depend upon the preferred transformation technique and the target species for transformation. For certain target species, different antibiotic or herbicide selection markers may be preferred. Selection markers used routinely in transformation include the nptII gene, which confers resistance to kanamycin and related antibiotics (Messing & Vierra. Gene 19: 259–268 (1982); Bevan et al., Nature 304: 184–187 (1983)), the bar gene, which confers resistance to the herbicide phosphinothricin (White et al., Nucl. Acids Res 18: 1062 (1990), Spencer et al. Theor. Appl. Genet 79: 625–631 (1990)), the hph gene, which confers resistance to the antibiotic hygromycin (Blochinger & Diggelmann, Mol Cell Biol 4: 2929–2931), and the dhfr gene, which confers resistance to methatrexate (Bourouis et al., EMBO J. 2(7): 1099–1104 (1983)), the EPSPS gene, which confers resistance to glyphosate (U.S. Pat. Nos. 4,940,935 and 5,188, 642), and the mannose-6-phosphate isomerase gene, which provides the ability to metabolize mannose (U.S. Pat. Nos. 5,767,378 and 5,994,629).

1. Vectors Suitable for *Agrobacterium* Transformation

Many vectors are available for transformation using *Agrobacterium tumefaciens*. These typically carry at least one T-DNA border sequence and include vectors such as pBIN19 (Bevan, Nucl. Acids Res. (1984)). Below, the construction of two typical vectors suitable for *Agrobacterium* transformation is described. Additional vectors suitable for *Agrobacterium*-mediated transformation are described in the Examples below a pCIB200 and pCIB2001:

The binary vectors pCIB200 and pCIB2001 are used for the construction of recombinant vectors for use with *Agrobacterium* and are constructed in the following manner. pTJS75kan is created by NarI digestion of pTJS75 (Schmidhauser & Helinski, J. Bacteriol. 164: 446–455 (1985)) allowing excision of the tetracycline-resistance gene, followed by insertion of an AccI fragment from pUC4K carrying an NPTII (Messing & Vierra, Gene 19: 259–268 (1982): Bevan et al., Nature 304: 184–187 (1983): McBride et al., Plant Molecular Biology 14: 266–276 (1990)). XhoI linkers are ligated to the EcoRV fragment of PCIB7 which contains the left and right T-DNA borders, a plant selectable nos/nptII chimeric gene and the pUC polylinker (Rothstein et al., Gene 53: 153–161 (1987)), and the XhoI-digested fragment are cloned into SalI-digested pTJS75kan to create pCIB200 (see also EP 0 332 104, example 19). pCIB200 contains the following unique polylinker restriction sites: EcoRI, SstI, KpnI, BglII, XbaI, and SalI. pCIB2001 is a derivative of pCIB200 created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for *Agrobacterium*-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

b. pCIB10 and Hygromycin Selection Derivatives thereof:

The binary vector pCIB10 contains a gene encoding kanamycin resistance for selection in plants and T-DNA right and left border sequences and incorporates sequences from the wide host-range plasmid pRK252 allowing it to replicate in both *E. coli* and *Agrobacterium*. Its construction is described by Rothstein et al. (Gene 53: 153–161 (1987)). Various derivatives of pCIB10 are constructed which incorporate the gene for hygromycin B phosphotransferase described by Gritz et al. (Gene 25: 179–188 (1983)). These derivatives enable selection of transgenic plant cells on hygromycin only (pCIB743), or hygromycin and kanamycin (pCIB715, pCIB717).

2. Vectors Suitable for non-*Agrobacterium* Transformation

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on *Agrobacterium* include transformation via particle bombardment, protoplast uptake (e.g. PEG and electroporation) and microinjection. The choice of vector depends largely on the preferred selection for the species being transformed. Below, the construction of typical vectors suitable for non-*Agrobacterium* transformation is described. Further, additional examples of vectors for non-*Agrobacterium* transformation are described in Example 8.

a. pCIB3064:

pCIB3064 is a pUC-derived vector suitable for direct gene transfer techniques in combination with selection by the herbicide basta (or phosphinothricin). The plasmid pCIB246 comprises the CaMV 35S promoter in operational fusion to the *E. coli* GUS gene and the CaMV 35S transcriptional terminator and is described in the PCT published application WO 93/07278. The 35S promoter of this vector contains two ATG sequences 5' of the start site. These sites are mutated using standard PCR techniques in such a way as to remove the ATGs and generate the restriction sites SspI and PvuII. The new restriction sites are 96 and 37 bp away from the unique SalI site and 101 and 42 bp away from the actual start site. The resultant derivative of pCIB246 is designated pCIB3025. The GUS gene is then excised from pCIB3025 by digestion with SalI and SacI, the termini rendered blunt and religated to generate plasmid pCIB3060. The plasmid pJIT82 is obtained from the John Innes Centre, Norwich and the a 400 bp SmaI fragment containing the bar gene from *Streptomyces* viridochromogenes is excised and inserted into the HpaI site of pCIB3060 (Thompson et al. EMBO J. 6: 2519–2523 (1987)). This generated pCIB3064, which comprises the bar gene under the control of the CaMV 35S promoter and terminator for herbicide selection, a gene for ampicillin resistance (for selection in *E. coli*) and a polylinker with the unique sites SphI, PstI, HindIII, and BamHI. This vector is suitable for the cloning of plant expression cassettes containing their own regulatory signals.

b. pSOG19 and pSOG35:

pSOG35 is a transformation vector that utilizes the *E. coli* gene dihydrofolate reductase (DFR) as a selectable marker conferring resistance to methotrexate. PCR is used to amplify the 35S promoter (~800 bp), intron 6 from the maize AdhI gene (~550 bp) and 18 bp of the GUS untranslated leader sequence from pSOG10. A 250-bp fragment encoding the *E. coli* dihydrofolate reductase type II gene is also amplified by PCR and these two PCR fragments are assembled with a SacI-PstI fragment from pB1221 (Clontech) which comprises the pUC19 vector backbone and the nopaline synthase terminator. Assembly of these fragments generates pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generates the vector pSOG35. pSOG19 and pSOG35 carry the pUC gene for ampicillin resistance and have HindIII, SphI, PstI and EcoRI sites available for the cloning of foreign substances.

3. Vector Suitable for Chloroplast Transformation

For expression of a nucleotide sequence of the present invention in plant plastids, plastid transformation vector pPH143 (WO 97/32011, example 36) is used. The nucleotide sequence is inserted into pPH143 thereby replacing the PROTOX coding sequence. This vector is then used for plastid transformation and selection of transformants for spectinomycin resistance. Alternatively, the nucleotide sequence is inserted in pPH143 so that it replaces the aadH gene. In this case, transformants are selected for resistance to PROTOX inhibitors.

D. Transformation

Once a nucleic acid sequence of the invention has been cloned into an expression system, it is transformed into a plant cell. The receptor and target expression cassettes of the present invention can be introduced into the plant cell in a number of art-recognized ways. Methods for regeneration of plants are also well known in the art. For example, Ti plasmid vectors have been utilized for the delivery of foreign DNA, as well as direct DNA uptake, liposomes, electroporation, microinjection, and microprojectiles. In addition, bacteria from the genus *Agrobacterium* can be utilized to transform plant cells. Below are descriptions of representative techniques for transforming both dicotyledonous and monocotyledonous plants, as well as a representative plastid transformation technique.

The method of transformation used is not critical to the instant invention and various methods of transformation are known. Newer transformation methods developed to transform plants or plant c ells may be applied as well. Therefore, any method which provide effective transformation may be used.

1. Transformation of Dicotyledons

Transformation techniques for dicotyledons are well known in the art and include *Agrobacterium*-based techniques and techniques that do not require *Agrobacterium*. Non-*Agrobacterium* techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., EMBO J. 3: 2717–2722 (1984), Potrykus et al., Mol. Gen. Genet. 199: 169–177 (1985), Reich et al., Biotechnology 4: 1001–1004 (1986), and Klein et al., Nature 327: 70–73 (1987). In each case the transformed cells are regenerated to whole plants using standard techniques known in the art.

*Agrobacterium*-mediated transformation is a preferred technique for transformation of dicotyledons because of its high efficiency of transformation and its broad utility with many different species. *Agrobacterium* transformation typically involves the transfer of the binary vector carrying the foreign DNA of interest (e.g. pCIB200 or pCIB2001) to an appropriate *Agrobacterium* strain which may depend of the complement of vir genes carried by the host *Agrobacterium* strain either on a co-resident Ti plasmid or chromosomally (e.g. strain CIB542 for pCIB200 and pCIB2001 (Uknes et al. Plant Cell 5: 159–169 (1993)). The transfer of the recombinant binary vector to *Agrobacterium* is accomplished by a triparental mating procedure using *E. coli* carrying the recombinant binary vector, a helper *E. coli* strain which carries a plasmid such as pRK2013 and which is able to mobilize the recombinant binary vector to the target *Agrobacterium* strain. Alternatively, the recombinant binary vector can be transferred to *Agrobacterium* by DNA transformation (Hofgen & Willmitzer, Nucl. Acids Res. 16: 9877 (1988)).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050, 5,036,006, and 5,100,792 all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

2. Transformation of Monocotyledons

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4: 1093–1096 (1986)).

Patent Applications EP 0 292 435, EP 0 392 225, and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. (Plant Cell 2: 603–618 (1990)) and Fromm et al. (Biotechnology 8: 833–839 (1990)) have published techniques for transformation of A188-derived maize line using particle bombardment. Furthermore, WO 93/07278 and Koziel et al. (Biotechnology 11: 194–200 (1993)) describe techniques for the transformation of elite inbred lines of maize by particle bombardment. This technique utilizes immature maize embryos of 1.5–2.5 mm length excised from a maize ear 14–15 days after pollination and a PDS-1000He Biolistics device for bombardment.

Transformation of rice can also be undertaken by direct gene transfer techniques utilizing protoplasts or particle bombardment. Protoplast-mediated transformation has been described for japonica-types and indica-types (Zhang et al. Plant Cell Rep 7: 379–384 (1988); Shimamoto et al. Nature 338: 274–277 (1989); Datta et al. Biotechnology 8: 736–740 (1990)). Both types are also routinely transformable using particle bombardment (Christou et al. Biotechnology 9: 957–962 (1991)). Furthermore, WO 93/21335 describes techniques for the transformation of rice via electroporation.

Patent Application EP 0 332 581 describes techniques for the generation, transformation and regeneration of *Pooideae* protoplasts. These techniques allow the transformation of *Dactylis* and wheat. Furthermore, wheat transformation has been described by Vasil et al. (Biotechnology 10: 667–674 (1992)) using particle bombardment into cells of type C long-term regenerable callus, and also by Vasil et al. (Biotechnology 11: 1553–1558 (1993)) and Weeks et al. (Plant Physiol. 102: 1077–1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75–1 mm in length) are plated onto MS medium with 3% sucrose (Murashige & Skoog, Physiologia Plantarum 15: 473–497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2–3 hours and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics® helium device using a burst pressure of ~1000 psi using a standard 80 mesh screen. After bombardment, the embryos are placed back into the dark to recover for about 24 hours (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Tranformation of monocotyledons using *Agrobacterium* has also been described. See, WO 94/00977 and U.S. Pat. No. 5,591,616, both of which are incorporated herein by reference. See also, Negrolto et al., *Plant Cell Reports* 19: 798–803 (2000), incorporated herein by reference.

For this example, rice (*Oryza sativa*) is used for generating transgenic plants. Various rice cultivars can be used (Hiei et al., 1994, Plant Journal 6:271–282; Dong et al., 1996, Molecular Breeding 2:267–276; Hiei et al., 1997, Plant Molecular Biology, 35:205–218). Also, the various media constituents described below may be either varied in quantity or substituted. Embryogenic responses are initiated and/or cultures are established from mature embryos by culturing on MS-CIM medium (MS basal salts, 4.3 g/liter; B5 vitamins (200×), 5 ml/liter; Sucrose, 30 g/liter; proline, 500 mg/liter; glutamine, 500 mg/liter; casein hydrolysate, 300 mg/liter; 2,4-D (1 mg/ml), 2 mvliter; adjust pH to 5.8 with 1 N KOH; Phytagel, 3 g/liter). Either mature embryos at the initial stages of culture response or established culture lines are inoculated and co-cultivated with the *Agrobacterium tumefaciens* strain LBA4404 (*Agrobacterium*) containing the desired vector construction. *Agrobacterium* is cultured from glycerol stocks on solid YPC medium (100 mg/L spectinomycin and any other appropriate antibiotic) for ~2 days at 28° C. *Agrobacterium* is re-suspended in liquid MS-CIM medium. The *Agrobacterium* culture is diluted to an OD600 of 0.2–0.3 and acetosyringone is added to a final concentration of 200 uM. Acetosyringone is added before mixing the solution with the rice cultures to induce *Agrobacterium* for DNA transfer to the plant cells. For inoculation, the plant cultures are immersed in the bacterial suspension. The liquid bacterial suspension is removed and the inoculated cultures are placed on co-cultivation medium and incubated at 22° C. for two days. The cultures are then transferred to MS-CIM medium with Ticarcillin (400 mg/liter) to inhibit the growth of *Agrobacterium*. For constructs utilizing the PMI selectable marker gene (Reed et al., In Vitro Cell. Dev. Biol.-Plant 37:127–132), cultures are transferred to selection medium containing Mannose as a carbohydrate source (MS with 2% Mannose, 300 mg/liter Ticarcillin) after 7 days, and cultured for 3–4 weeks in the dark. Resistant colonies are then transferred to regeneration induction medium (MS with no 2,4-D, 0.5 mg/liter IAA, 1 mg/liter zeatin, 200 mg/liter timentin 2% Mannose and 3% Sorbitol) and grown in the dark for 14 days. Proliferating colonies are then transferred to another round of regeneration induction media and moved to the light growth room. Regenerated shoots are transferred to GA7 containers with GA7-1 medium (MS with no hormones and 2% Sorbitol) for 2 weeks and then moved to the greenhouse when they are large enough and have adequate roots. Plants are transplanted to soil in the greenhouse ($T_0$ generation) grown to maturity, and the $T_1$ seed is harvested.

3. Transformation of Plastids

Seeds of *Nicotiana tabacum* c.v. 'Xanthi nc' are germinated seven per plate in a 1" circular array on T agar medium and bombarded 12–14 days after sowing with 1 μm tungsten particles (M10, Biorad, Hercules, Calif.) coated with DNA from plasmids pPH143 and pPH145 essentially as described (Svab, Z. and Maliga, P. (1993) PNAS 90, 913–917). Bombarded seedlings are incubated on T medium for two days after which leaves are excised and placed abaxial side up in bright light (350–500 μmol photons/m$^2$/s) on plates of RMOP medium (Svab, Z., Hajdukiewicz, P. and Maliga, P. (1990) PNAS 87, 8526–8530) containing 500 μg/ml spectinomycin dihydrochloride (Sigma, St. Louis, Mo.). Resistant shoots appearing underneath the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (Sambrook et al., (1989) *Molecular Cloning: A Laboratory Manual*, Cold Spring Harbor Laboratory, Cold Spring Harbor). BamHI/EcoRI-digested total cellular DNA (Mettler, I. J. (1987) *Plant Mol Biol Reporter* 5, 346–349) is separated on 1% Tris-borate (TBE) agarose gels, transferred to nylon membranes (Amersham) and probed with $^{32}$P-labeled random primed DNA sequences corresponding to a 0.7 kb BamHI/HindIII DNA fragment from pC8 containing a portion of the rps7/12 plastid targeting sequence. Homoplasmic shoots are rooted aseptically on spectinomycin-containing MS/IBA medium (McBride, K. E. et al. (1994) *PNAS* 91, 7301–7305) and transferred to the greenhouse.

V. Breeding and Seed Production

A. Breeding

The plants obtained via tranformation with a nucleic acid sequence of the present invention can be any of a wide variety of plant species, including those of monocots and dicots; however, the plants used in the method of the invention are preferably selected from the list of agronomically important target crops set forth supra. The expression of a gene of the present invention in combination with other characteristics important for production and quality can be incorporated into plant lines through breeding. Breeding approaches and techniques are known in the art. See, for example, Welsh J. R., *Fundamentals of Plant Genetics and Breeding*, John Wiley & Sons, NY (1981); *Crop Breeding*, Wood D. R. (Ed.) American Society of Agronomy Madison, Wis. (1983); Mayo O., *The Theory of Plant Breeding*, Second Edition, Clarendon Press, Oxford (1987); Singh, D. P., *Breeding for Resistance to Diseases and Insect Pests*, Springer-Verlag, NY (1986); and Wricke and Weber, *Quantitative Genetics and Selection Plant Breeding*, Walter de Gruyter and Co., Berlin (1986).

The genetic properties engineered into the transgenic seeds and plants described above are passed on by sexual reproduction or vegetative growth and can thus be maintained and propagated in progeny plants. Generally said maintenance and propagation make use of known agricultural methods developed to fit specific purposes such as tilling, sowing or harvesting. Specialized processes such as hydroponics or greenhouse technologies can also be applied. As the growing crop is vulnerable to attack and damages caused by insects or infections as well as to competition by weed plants, measures are undertaken to control weeds, plant diseases, insects, nematodes, and other adverse conditions to improve yield. These include mechanical measures such a tillage of the soil or removal of weeds and infected plants, as well as the application of agrochemicals such as herbicides, fungicides, gametocides, nematicides, growth regulants, ripening agents and insecticides.

Use of the advantageous genetic properties of the transgenic plants and seeds according to the invention can further be made in plant breeding, which aims at the development of plants with improved properties such as tolerance of pests, herbicides, or stress, improved nutritional value, increased yield, or improved structure causing less loss from lodging or shattering. The various breeding steps are characterized by well-defined human intervention such as selecting the lines to be crossed, directing pollination of the parental lines, or selecting appropriate progeny plants. Depending on the desired properties, different breeding measures are taken. The relevant techniques are well known in the art and include but are not limited to hybridization, inbreeding, backcross breeding, multiline breeding, variety blend, interspecific hybridization, aneuploid techniques, etc. Hybridization techniques also include the sterilization of plants to yield male or female sterile plants by mechanical, chemical, or biochemical means. Cross pollination of a male sterile plant with pollen of a different line assures that the genome of the male sterile but female fertile plant will uniformly obtain properties of both parental lines. Thus, the transgenic seeds and plants according to the invention can be used for the breeding of improved plant lines, that for example, increase the effectiveness of conventional methods such as herbicide or pesticide treatment or allow one to dispense with said methods due to their modified genetic properties. Alternatively new crops with improved stress tolerance can be obtained, which, due to their optimized genetic "equipment", yield harvested product of better quality than products that were not able to tolerate comparable adverse developmental conditions.

B. Seed Production

In seed production, germination quality and uniformity of seeds are essential product characteristics. As it is difficult to keep a crop free from other crop and weed seeds, to control seedborne diseases, and to produce seed with good germination, fairly extensive and well-defined seed production practices have been developed by seed producers, who are experienced in the art of growing, conditioning and marketing of pure seed. Thus, it is common practice for the farmer to buy certified seed meeting specific quality standards instead of using seed harvested from his own crop. Propagation material to be used as seeds is customarily treated with a protectant coating comprising herbicides, insecticides, fungicides, bactericides, nematicides, molluscicides, or mixtures thereof. Customarily used protectant coatings comprise compounds such as captan, carboxin, thiram (TMTD®), methalaxyl (Apron®), and pirimiphos-methyl (Actellic®). If desired, these compounds are formulated together with further carriers, surfactants or application-promoting adjuvants customarily employed in the art of formulation to provide protection against damage caused by bacterial, fungal or animal pests. The protectant coatings may be applied by impregnating propagation material with a liquid formulation or by coating with a combined wet or dry formulation. Other methods of application are also possible such as treatment directed at the buds or the fruit.

VI. Alteration of Expression of Nucleic Acid Molecules

The alteration in expression of the nucleic acid molecules of the present invention is achieved in one of the following ways:

A. "Sense" Suppression

Alteration of the expression of a nucleotide sequence of the present invention, preferably reduction of its expression, is obtained by "sense" suppression (referenced in e.g. Jorgensen et al. (1996) Plant Mol. Biol. 31, 957–973). In this case, the entirety or a portion of a nucleotide sequence of the present invention is comprised in a DNA molecule. The DNA molecule is preferably operatively linked to a promoter functional in a cell comprising the target gene, preferably a plant cell, and introduced into the cell, in which the nucleotide sequence is expressible. The nucleotide sequence is inserted in the DNA molecule in the "sense orientation", meaning that the coding strand of the nucleotide sequence can be transcribed. In a preferred embodiment, the nucleotide sequence is fully translatable and all the genetic information comprised in the nucleotide sequence, or portion thereof, is translated into a polypeptide. In another preferred embodiment, the nucleotide sequence is partially translatable and a short peptide is translated. In a preferred embodiment, this is achieved by inserting at least one premature stop codon in the nucleotide sequence, which bring translation to a halt. In another more preferred embodiment, the nucleotide sequence is transcribed but no translation product is being made. This is usually achieved by removing the start codon, e.g. the "ATG", of the polypeptide encoded by the nucleotide sequence. In a further preferred embodiment, the DNA molecule comprising the nucleotide sequence, or a portion thereof, is stably integrated in the genome of the plant cell. In another preferred embodiment, the DNA molecule comprising the nucleotide sequence, or a portion thereof, is comprised in an extrachromosomally replicating molecule.

In transgenic plants containing one of the DNA molecules described immediately above, the expression of the nucleotide sequence corresponding to the nucleotide sequence comprised in the DNA molecule is preferably reduced. Preferably, the nucleotide sequence in the DNA molecule is at least 70% identical to the nucleotide sequence the expression of which is reduced, more preferably it is at least 80% identical, yet more preferably at least 90% identical, yet more preferably at least 95% identical, yet more preferably at least 99% identical.

B. "Anti-sense" Suppression

In another preferred embodiment, the alteration of the expression of a nucleotide sequence of the present invention, preferably the reduction of its expression is obtained by "anti-sense" suppression. The entirety or a portion of a nucleotide sequence of the present invention is comprised in a DNA molecule. The DNA molecule is preferably operatively linked to a promoter functional in a plant cell, and introduced in a plant cell, in which the nucleotide sequence is expressible. The nucleotide sequence is inserted in the DNA molecule in the "anti-sense orientation", meaning that the reverse complement (also called sometimes non-coding strand) of the nucleotide sequence can be transcribed. In a preferred embodiment, the DNA molecule comprising the nucleotide sequence, or a portion thereof, is stably integrated in the genome of the plant cell. In another preferred embodiment the DNA molecule comprising the nucleotide sequence, or a portion thereof, is comprised in an extrachromosomally replicating molecule. Several publications describing this approach are cited for further illustration (Green, P. J. et al., Ann. Rev. Biochem. 55:569–597 (1986); van der Krol, A. R. et al, Antisense Nuc. Acids & Proteins, pp. 125–141 (1991); Abel, P. P. et al., PNAS 86:6949–6952 (1989); Ecker, J. R. et al., PNAS 83:5372–5376 (August 1986)).

In transgenic plants containing one of the DNA molecules described immediately above, the expression of the nucleotide sequence corresponding to the nucleotide sequence comprised in the DNA molecule is preferably reduced. Preferably, the nucleotide sequence in the DNA molecule is at least 70% identical to the nucleotide sequence the expression of which is reduced, more preferably it is at least 80% identical, yet more preferably at least 90% identical, yet more preferably at least 95% identical, yet more preferably at least 99% identical. Antisense suppression of the RAR1 nucleic acid molecules of the invention is more specifically described below in Example 5.

C. Homologous Recombination

In another preferred embodiment, at least one genomic copy corresponding to a nucleotide sequence of the present invention is modified in the genome of the plant by homologous recombination as further illustrated in Paszkowski et al., EMBO Journal 7:4021–26 (1988). This technique uses the property of homologous sequences to recognize each other and to exchange nucleotide sequences between each by a process known in the art as homologous recombination. Homologous recombination can occur between the chromosomal copy of a nucleotide sequence in a cell and an incoming copy of the nucleotide sequence introduced in the cell by transformation. Specific modifications are thus accurately introduced in the chromosomal copy of the nucleotide sequence. In one embodiment, the regulatory elements of the nucleotide sequence of the present invention are modified. Such regulatory elements are easily obtainable by screening a genomic library using the nucleotide sequence of the present invention, or a portion thereof, as a probe. The existing regulatory elements are replaced by different regulatory elements, thus altering expression of the nucleotide sequence, or they are mutated or deleted, thus abolishing the expression of the nucleotide sequence. In another embodiment, the nucleotide sequence is modified by deletion of a part of the nucleotide sequence or the entire nucleotide sequence, or by mutation. Expression of a mutated polypeptide in a plant cell is also contemplated in the present invention. More recent refinements of this technique to disrupt endogenous plant genes have been described (Kempin et al., Nature 389: 802–803 (1997) and Miao and Lam, Plant J., 7:359–365 (1995).

In another preferred embodiment, a mutation in the chromosomal copy of a nucleotide sequence is introduced by transforming a cell with a chimeric oligonucleotide composed of a contiguous stretch of RNA and DNA residues in a duplex conformation with double hairpin caps on the ends. An additional feature of the oligonucleotide is for example the presence of 2'-O-methylation at the RNA residues. The RNA/DNA sequence is designed to align with the sequence of a chromosomal copy of a nucleotide sequence of the present invention and to contain the desired nucleotide change. For example, this technique is further illustrated in U.S. Pat. No. 5,501,967 and Zhu et al. (1999) Proc. Natl. Acad. Sci. USA 96: 8768–8773.

D. Ribozymes

In a further embodiment, the RNA coding for a polypeptide of the present invention is cleaved by a catalytic RNA, or ribozyme, specific for such RNA. The ribozyme is expressed in transgenic plants and results in reduced amounts of RNA coding for the polypeptide of the present invention in plant cells, thus leading to reduced amounts of polypeptide accumulated in the cells. This method is further illustrated in U.S. Pat. No. 4,987,071.

E. Dominant-Negative Mutants

In another preferred embodiment, the activity of the polypeptide encoded by the nucleotide sequences of this invention is changed. This is achieved by expression of dominant negative mutants of the proteins in transgenic plants, leading to the loss of activity of the endogenous protein.

F. Aptamers

In a further embodiment, the activity of polypeptide of the present invention is inhibited by expressing in transgenic plants nucleic acid ligands, so-called aptamers, which specifically bind to the protein. Aptamers are preferentially obtained by the SELEX (Systematic Evolution of Ligands by EXponential Enrichment) method. In the SELEX method, a candidate mixture of single stranded nucleic acids having regions of randomized sequence is contacted with the protein and those nucleic acids having an increased affinity to the target are partitioned from the remainder of the candidate mixture. The partitioned nucleic acids are amplified to yield a ligand enriched mixture. After several iterations a nucleic acid with optimal affinity to the polypeptide is obtained and is used for expression in transgenic plants. This method is further illustrated in U.S. Pat. No. 5,270,163.

G. Zinc Finger Proteins

A zinc finger protein that binds a nucleotide sequence of the present invention or to its regulatory region is also used to alter expression of the nucleotide sequence. Preferably, transcription of the nucleotide sequence is reduced or increased. Zinc finger proteins are for example described in Beerli et al. (1998) PNAS 95:14628–14633, or in WO 95/19431, WO 98/54311, or WO 96/06166, all incorporated herein by reference in their entirety.

H. dsRNA

In another preferred embodiment, the alteration of the expression of a nucleotide sequence of the present invention, preferably the reduction of its expression, is obtained by double-stranded RNA (dsRNA) interference. The entirety or, preferably a portion of a nucleotide sequence of the present invention is comprised in a DNA molecule. The size of the DNA molecule is preferably from 100 to 1000 nucleotides or more; the optimal size to be determined empirically. Two copies of the identical DNA molecule are linked, separated by a spacer DNA molecule, such that the first and second copies are in opposite orientations. In the preferred embodiment, the first copy of the DNA molecule is in the reverse complement (also known as the non-coding strand) and the second copy is the coding strand; in the most preferred embodiment, the first copy is the coding strand, and the second copy is the reverse complement. The size of the spacer DNA molecule is preferably 200 to 10,000 nucleotides, more preferably 400 to 5000 nucleotides and most preferably 600 to 1500 nucleotides in length. The spacer is preferably a random piece of DNA, more preferably a random piece of DNA without homology to the target organism for dsRNA interference, and most preferably a functional intron which is effectively spliced by the target organism. The two copies of the DNA molecule separated by the spacer are operatively linked to a promoter functional in a plant cell, and introduced in a plant cell, in which the nucleotide sequence is expressible. In a preferred embodiment, the DNA molecule comprising the nucleotide sequence, or a portion thereof, is stably integrated in the genome of the plant cell. In another preferred embodiment the DNA molecule comprising the nucleotide sequence, or a portion thereof, is comprised in an extrachromosomally replicating molecule. Several publications describing this approach are cited for further illustration (Waterhouse et al. (1998) PNAS 95:13959–13964; Chuang and Meyerowitz (2000) PNAS 97:4985–4990; Smith et al. (2000) Nature 407:319–320). Alteration of the expression of a nucleotide sequence by dsRNA interference is also described in, for example WO 99/32619, WO 99/53050 or WO 99/61631, all incorporated herein by reference in their entirety.

In transgenic plants containing one of the DNA molecules described immediately above, the expression of the nucleotide sequence corresponding to the nucleotide sequence comprised in the DNA molecule is preferably reduced. Preferably, the nucleotide sequence in the DNA molecule is at least 70% identical to the nucleotide sequence the expression of which is reduced, more preferably it is at least 80% identical, yet more preferably at least 90% identical, yet more preferably at least 95% identical, yet more preferably at least 99% identical.

An example of dsRNA interference of the RAR1 nucleic acid molecules of the invention is set forth in Example 5.

I. Insertion of a DNA Molecule (Insertional Mutagenesis)

In another preferred embodiment, a DNA molecule is inserted into a chromosomal copy of a nucleotide sequence of the present invention, or into a regulatory region thereof. Preferably, such DNA molecule comprises a transposable element capable of transposition in a plant cell, such as e.g. Ac/Ds, Em/Spm, mutator. Alternatively, the DNA molecule comprises a T-DNA border of an *Agrobacterium* T-DNA. The DNA molecule may also comprise a recombinase or integrase recognition site which can be used to remove part of the DNA molecule from the chromosome of the plant cell. An example of this method is described in Example 4. Methods of insertional mutagenesis using T-DNA, transposons, oligonucleotides or other methods known to those skilled in the art are also encompassed. Methods of using T-DNA and transposon for insertional mutagenesis are described in Winkler et al. (1989) Methods Mol. Biol. 82:129–136 and Martienssen (1998) PNAS 95:2021–2026, incorporated herein by reference in their entireties.

J. Deletion mutagenesis

In yet another embodiment, a mutation of a nucleic acid molecule of the present invention is created in the genomic copy of the sequence in the cell or plant by deletion of a portion of the nucleotide sequence or regulator sequence. Methods of deletion mutagenesis are known to those skilled in the art. See, for example, Miao et al, (1995) Plant J. 7:359.

In yet another embodiment, this deletion is created at random in a large population of plants by chemical mutagenesis or irradiation and a plant with a deletion in a gene of the present invention is isolated by forward or reverse genetics. Irradiation with fast neutrons or gamma rays is known to cause deletion mutations in plants (Silverstone et al, (1998) Plant Cell, 10:155–169; Bruggemann et al., (1996) Plant J., 10:755–760; Redei and Koncz in *Methods in Arabidopsis Research*, World Scientific Press (1992), pp. 16–82). Deletion mutations in a gene of the present invention can be recovered in a reverse genetics strategy using PCR with pooled sets of genomic DNAs as has been shown in *C. elegans* (Liu et al., (1999), Genome Research, 9:859–867.). A forward genetics strategy would involve mutagenesis of a line displaying PTGS followed by screening the M2 progeny for the absence of PTGS. Among these mutants would be expected to be some that disrupt a gene of the present invention. This could be assessed by Southern blot or PCR for a gene of the present invention with genomic DNA from these mutants.

K. Overexpression in a Plant Cell

In yet another preferred embodiment, a nucleotide sequence of the present invention encoding a rice RAR1 polypeptide and/or activity in a plant cell is over-expressed. Examples of nucleic acid molecules and expression cassettes for over-expression of a nucleic acid molecule of the present invention are described above. Methods known to those skilled in the art of over-expression of nucleic acid molecules are also encompassed by the present invention.

In a preferred embodiment, the expression of the nucleotide sequence of the present invention is altered in every cell of a plant. This is for example obtained though homologous recombination or by insertion in the chromosome. This is also for example obtained by expressing a sense or antisense RNA, zinc finger protein or ribozyme under the control of a promoter capable of expressing the sense or antisense RNA, zinc finger protein or ribozyme in every cell of a plant. Constitutive expression, inducible, tissue-specific or developmentally-regulated expression are also within the scope of the present invention and result in a constitutive, inducible, tissue-specific or developmentally-regulated alteration of the expression of a nucleotide sequence of the present invention in the plant cell. Constructs for expression of the sense or antisense RNA, zinc finger protein or ribozyme, or for over-expression of a nucleotide sequence of the present invention, are prepared and transformed into a plant cell according to the teachings of the present invention, e.g. as described infra. An description of over-expression is described below in Examples 1–3 and 6–7.

VII. Polypeptides

The present invention further relates to isolated polypeptides comprising the amino acid sequence of SEQ ID NO:2. In particular, isolated polypeptides comprising the amino acid sequence of SEQ ID NO:2, and variants having conservative amino acid modifications. One skilled in the art will recognize that individual substitutions, deletions or additions to a nucleic acid, peptide, polypeptide or protein sequence which alters, adds or deletes a single amino acid or a small percent of amino acids in the encoded sequence is a "conservative modification" where the modification results in the substitution of an amino acid with a chemically similar amino acid. Conservative modified variants provide similar biological activity as the unmodified polypeptide. Conservative substitution tables listing functionally similar amino acids are known in the art. See Crighton (1984) *Proteins*, W.H. Freeman and Company.

In a preferred embodiment, a polypeptide having substantial similarity to a polypeptide sequence listed in SEQ ID NO:2, or exon, domain, or feature thereof, is an allelic variant of the polypeptide sequence listed in SEQ ID NO:2. In another preferred embodiment, a polypeptide having substantial similarity to a polypeptide sequence listed in SEQ ID NO:2, or exon, domain, or feature thereof, is a naturally occurring variant of the polypeptide sequence listed in SEQ ID NO:2. In another preferred embodiment, a polypeptide having substantial similarity to a polypeptide sequence listed in SEQ ID NO:2, or exon, domain, or feature thereof, is a polymorphic variant of the polypeptide sequence listed in SEQ ID NO:2.

In an alternate preferred embodiment, the sequence having substantial similarity contains a deletion or insertion of at least one amino acid. In a more preferred embodiment, the deletion or insertion is of less than about ten amino acids. In a most preferred embodiment, the deletion or insertion is of less than about three amino acids.

In a preferred embodiment, the sequence having substantial similarity encodes a substitution in at least one amino acid.

Embodiments of the present invention also contemplate an isolated polypeptide containing a polypeptide sequence including:

(a) a polypeptide sequence listed in SEQ ID NO:2, or exon, domain, or feature thereof;

(b) a polypeptide sequence having substantial similarity to (a);

(c) a polypeptide sequence encoded by a nucleotide sequence identical to or having substantial similarity to a nucleotide sequence listed in SEQ ID NO:1, or an exon, domain, or feature thereof, or a sequence complementary thereto;

(d) a polypeptide sequence encoded by a nucleotide sequence capable of hybridizing under medium stringency conditions to a nucleotide sequence listed in SEQ ID NO:1, or to a sequence complementary thereto; and (e) a functional fragment of (a), (b), (c) or (d).

In another preferred embodiment, the polypeptide having substantial similarity is an allelic variant of a polypeptide sequence listed in SEQ ID NO:2, or a fragment, domain, repeat, feature, or chimeras thereof. In another preferred embodiment, the isolated nucleic acid includes a plurality of regions from the polypeptide sequence encoded by a nucleotide sequence identical to or having substantial similarity to a nucleotide sequence listed in SEQ ID NO:1, or fragment, domain, or feature thereof, or a sequence complementary thereto. In another preferred embodiment, the polypeptide is a functional fragment or domain. In yet another preferred embodiment, the polypeptide is a chimera, where the chimera may include functional protein domains, including domains, repeats, post-translational modification sites, or other features. In a more preferred embodiment, the polypeptide is a plant polypeptide. In a more preferred embodiment, the plant is a dicot. In a more preferred embodiment, the plant is a gymnosperm. In a more preferred embodiment, the plant is a monocot. In a more preferred embodiment, the monocot is a cereal. In a more preferred embodiment, the cereal may be, for example, maize, wheat, barley, oats, rye, millet, sorghum, triticale, secale, einkorn, spelt, emmer, teff, milo, flax, gramma grass, *Tripsacum*, and teosinte. In a most preferred embodiment, the cereal is rice.

In a preferred embodiment, the polypeptide is expressed in a specific location or tissue of a plant. In a more preferred embodiment, the location or tissue is for example, but not limited to, epidermis, vascular tissue, meristem, cambium, cortex or pith. In a most preferred embodiment, the location or tissue is leaf or sheath, root, flower, and developing ovule or seed.

In a preferred embodiment, the polypeptide sequence encoded by a nucleotide sequence having substantial similarity to a nucleotide sequence listed in SEQ ID NO:1 or a fragment, domain, or feature thereof or a sequence complementary thereto, includes a deletion or insertion of at least one nucleotide. In a more preferred embodiment, the deletion or insertion is of less than about thirty nucleotides. In a most preferred embodiment, the deletion or insertion is of less than about five nucleotides.

In a preferred embodiment, the polypeptide sequence encoded by a nucleotide sequence having substantial similarity to a nucleotide sequence listed in SEQ ID NO:1, or fragment, domain, or feature thereof or a sequence complementary thereto, includes a substitution of at least one codon. In a more preferred embodiment, the substitution is conservative.

In a preferred embodiment, the polypeptide sequences having substantial similarity to the polypeptide sequence listed in SEQ ID NO:2, or a fragment, domain, repeat, feature, or chimeras thereof includes a deletion or insertion of at least one amino acid.

The polypeptides of the invention, fragments thereof or variants thereof can comprise any number of contiguous amino acid residues from a polypeptide of the invention, wherein the number of residues is selected from the group of integers consisting of from 10 to the number of residues in a full-length polypeptide of the invention. Preferably, the portion or fragment of the polypeptide is functional as a RAR1 protein in the diseases resistance signaling pathway. The present invention includes active polypeptides having specific activity of at least 20%, 30%, or 40%, and preferably at least 505, 60%, or 70%, and most preferably at least 805, 90% or 95% that of the native (non-synthetic) endogenous polypeptide. Further, the substrate specificity ($k_{cat}/K_m$) is optionally substantially similar to the native (non-synthetic), endogenous polypeptide. Typically the $K_m$ will be at least 30%, 40%, or 50% of the native, endogenous polypeptide; and more preferably at least 605, 70%, 80%, or 90%. Methods of assaying and quantifying measures of activity and substrate specificity are well known to those of skill in the art.

The isolated polypeptides of the present invention will elicit production of an antibody specifically reactive to a polypeptide of the present invention when presented as an immunogen. Therefore, the polypeptides of the present invention can be employed as immunogens for constructing antibodies immunoreactive to a protein of the present invention for such purposes, but not limited to, immunoassays or protein purification techniques. Immunoassays for determining binding are well known to those of skill in the art such as, but not limited to, ELISAs or competitive immunoassays. The present invention further relates to an antibody that binds to the polypeptides of the invention, in particular, to the polypeptide of SEQ ID NO:2.

The polypeptides of the present invention are also useful to determine DNA binding domains of the RAR1 type proteins. DNA binding assays and DNA footprinting assays are known to those skilled in the art. The polypeptides of the present invention are also useful for isolating RAR1 regulatory regions, and R genes for which their expression is affected by the RAR1 protein. Isolating such regulatory domains which may or maynot include promoters or enhancers are known to those skilled in the art.

Embodiments of the present invention also relate to chimeric polypeptides encoded by the isolated nucleic acid molecules of the present disclosure including a chimeric polypeptide containing a polypeptide sequence encoded by an isolated nucleic acid containing a nucleotide sequence including:
(a) a nucleotide sequence listed in SEQ ID NO:1, or exon, domain, or feature thereof;
(b) a nucleotide sequence having substantial similarity to (a);
(c) a nucleotide sequence capable of hybridizing to (a);
(d) a nucleotide sequence complementary to (a), (b) or (c); and
(e) a nucleotide sequence which is the reverse complement of (a), (b) or (c);
(f) or a functional fragment thereof.

A polypeptide containing a polypeptide sequence encoded by an isolated nucleic acid containing a nucleotide sequence, its complement, or its reverse complement, encoding a polypeptide including a polypeptide sequence including:
(a) a polypeptide sequence listed in SEQ ID NO:2, or a domain, repeat, feature, or chimeras thereof;
(b) a polypeptide sequence having substantial similarity to (a);
(c) a polypeptide sequence encoded by a nucleotide sequence identical to or having substantial similarity to a nucleotide sequence listed in SEQ ID NO:1, or an exon, domain, or feature thereof, or a sequence complementary thereto;
(d) a polypeptide sequence encoded by a nucleotide sequence capable of hybridizing under medium stringency conditions to a nucleotide sequence listed in SEQ ID NO:1, or to a sequence complementary thereto; and
(e) a functional fragment of (a), (b), (c) or (d);
(f) or a functional fragment thereof.

The isolated nucleic acid molecules of the present invention are useful for expressing a polypeptide of the present invention in a recombinantly engineered cell such as a bacteria, yeast, insect, mammalian or plant cell. The cells produce the polypeptide in a non-natural condition (e.g. in quantity, composition, location and/or time) because they have been genetically altered to do so. Those skilled in the art are knowledgeable in the numerous expression systems available for expression of nucleic acids encoding a protein of the present invention, and will not be described in detail below.

Briefly, the expression of isolated nucleic acids encoding a polypeptide of the invention will typically be achieved, for example, by operably linking the nucleic acid or cDNA to a promoter (constitutive or regulatable) followed by incorporation into an expression vector. The vectors are suitable for replication and/or integration in either prokaryotes or eukaryotes. Commonly used expression vectors comprise transcription and translation terminators, initiation sequences and promoters for regulation of the expression of the nucleic acid molecule encoding the polypeptide. To obtain high levels of expression of the cloned nucleic acid molecule, it is desirable to use expression vectors comprising a strong promoter to direct transcription, a ribosome binding site for translation initiation, and a transcription/translation terminator. One skilled in the art will recognize that modifications may be made to the polypeptide of the present invention without diminishing its biological activity. Some modifications may be made to facilitate the cloning, expression or incorporation of the polypeptide of the invention into a fusion protein. Such modification are well known in the art and include, but are not limited to, a methionine added at the amino terminus to provide an initiation site, or additiona amino acids (e.g. poly Histadine) placed on either terminus to create conveniently located purification sequences. Restriction sites or termination codons can also be introduced into the vector.

In a preferred embodiment, the expression vector includes one or more elements such as, for example, but not limited to, a promoter-enhancer sequence, a selection marker sequence, an origin of replication, an epitope-tag encoding sequence, or an affinity purification-tag encoding sequence. In a more preferred embodiment, the promoter-enhancer sequence may be, for example, the CaMV 35S promoter, the CaMV 19S promoter, the tobacco PR-1a promoter, the ubiquitin promoter, and the phaseolin promoter. In another embodiment, the promoter is operable in plants, and more preferably, a constitutive or inducible promoter. In another preferred embodiment, the selection marker sequence encodes an antibiotic resistance gene. In another preferred embodiment, the epitope-tag sequence encodes V5, the peptide Phe-His-His-Thr-Thr, hemagglutinin, or glutathione-S-transferase. In another preferred embodiment the affinity purification-tag sequence encodes a polyamino acid sequence or a polypeptide. In a more preferred embodiment, the polyamino acid sequence is polyhistidine. In a more preferred embodiment, the polypeptide is chitin binding domain or glutathione-S-transferase. In a more preferred embodiment, the affinity purification-tag sequence comprises an intein encoding sequence.

Prokaryotic cells may be used a host cells, for example, but not limited to, *Escherichia coli*, and other microbial strains known to those in the art. Methods for expressing proteins in prokaryotic cells are well known to those in the art and can be found in many laboratory manuals such as *Molecular Cloning: A Laboratory Manual*, by J. Sambrook et al. (1989, Cold Spring Harbor Laboratory Press). A variety of promoters, ribosome binding sites, and operators to control expression are available to those skilled in the art, as are selectable markers such as antibiotic resistance genes. The type of vector chosen is to allow for optimal growth and expression in the selected cell type.

A variety of eukaryotic expression systems are available such as, but not limited to, yeast, insect cell lines, plant cells and mammalian cells. Expression and synthesis of heterologous proteins in yeast is well known (see Sherman et al., *Methods in Yeast Genetics*, Cold Spring Harbor Laboratory Press, 1982). Commonly used yeast strains widely used for production of eukaryotic proteins are *Saccharomyces cerevisiae* and *Pichia pastoris*, and vectors, strains and protocols for expression are available from commercial suppliers (e.g., Invitrogen).

Mammalian cell systems may be transfected with expression vectors for production of proteins. Many suitable host cell lines are available to those in the art, such as, but not limited to the HEK293, BHK21 and CHO cells lines. Expression vectors for these cells can include expression control sequences such as an origin of replication, a promoter, (e.g., the CMV promoter, a HSV tk promoter or phosphoglycerate kinase (pgk) promoter), an enhancer, and protein processing sites such as ribosome binding sites, RNA splice sites, polyadenylation sites, and transcription terminator sequences. Other animal cell lines useful for the production of proteins are available commercially or from depositories such as the American Type Culture Collection.

Expression vectors for expressing proteins in insect cells are usually derived from the SF9 baculovirus or other viruses known in the art. A number of suitable insect cell lines are available including but not limited to, mosquito larvae, silkworm, armyworm, moth and *Drosophila* cell lines.

Methods of transfecting animal and lower eukaryotic cells are known. Numerous methods are used to make eukaryotic cells competent to introduce DNA such as but not limited to: calcium phosphate precipitation, fusion of the recipient cell with bacterial protoplasts containing the DNA, treatment of the recipient cells with liposomes containing the DNA, DEAE dextrin, electroporation, biolistics, and microinjection of the DNA directly into the cells. Tranfected cells are cultured using means well known in the art (see, Kuchler, R. J., *Biochemical Methods in Cell Culture and Virology*, Dowden, Hutchinson and Ross, Inc. 1997).

Once a polypeptide of the present invention is expressed it may be isolated and purified from the cells using methods known to those skilled in the art. The purification process may be monitored using Western blot techniques or radioimmunoassay or other standard immunoassay techniques. Protein purification techniques are commonly known and used by those in the art (see R. Scopes, *Protein Purification: Principles and Practice*, Springer-Verlag, New York 1982: Deutscher, *Guide to Protein Purification*, Academic Press (1990). Embodiments of the present invention provide a method of producing a recombinant protein in which the expression vector includes one or more elements including a promoter-enhancer sequence, a selection marker sequence, an origin of replication, an epitope-tag encoding sequence, and an affinity purification-tag encoding sequence. In one preferred embodiment, the nucleic acid construct includes an epitope-tag encoding sequence and the isolating step includes use of an antibody specific for the epitope-tag. In another preferred embodiment, the nucleic acid construct contains a polyamino acid encoding sequence and the isolating step includes use of a resin comprising a polyamino acid binding substance, preferably where the polyamino acid is polyhistidine and the polyamino binding resin is nickel-charged agarose resin. In yet another preferred embodiment, the nucleic acid construct contains a polypeptide encoding sequence and the isolating step includes the use of a resin containing a polypeptide binding substance, preferably where the polypeptide is a chitin binding domain and the resin contains chitin-sepharose.

The polypeptides of the present invention cam be synthesized using non-cellular synthetic methods known to those in the art. Techniques for solid phase synthesis are described by Barany and Mayfield, Solid-Phase Peptide Synthesis, pp. 3–284 in the Peptides: *Analysis, Synthesis, Biology, Vol. 2, Special Methods in Peptide Synthesis, Part A*; Merrifield, et al., *J. Am. Chem. Soc.* 85:2149–56 (1963) and Stewart et al., *Solid Phase Peptide Synthesis*, 2$^{nd}$ ed. Pierce Chem. Co., Rockford, Ill. (1984).

The present invention further provides a method for modifying (i.e. increasing or decreasing) the concentration or composition of the polypeptides of the invention in a plant or part thereof. Modification can be effected by increasing or decreasing the concentration and/or the composition (i.e. the ration of the polypeptides of the present invention) in a plant. The method comprised introducing into a plant cell with an expression cassette comprising a nucleic acid molecule of the present invention, or an nucleic acid encoding a RAR1 sequence as described above to obtain a transformed plant cell or tissue, culturing the transformed plant cell or tissue. The nucleic acid molecule can be under the regulation of a constitutive or inducible promoter. The method can further comprise inducing or repressing expression of a nucleic acid molecule of a RAR1 sequence in the plant for a time sufficient to modify the concentration and/or composition in the plant or plant part.

A plant or plant part having modified expression of a RAR1 nucleic acid molecule can be analyzed and selected using methods known to those skilled in the art such as, but not limited to, Southern blot, DNA sequencing, or PCR analysis using primers specific to the nucleic acid molecule and detecting amplicons produced therefrom.

In general, concentration or composition in increased or decreased by at least 5%, 10%, 20%, 30%, 40%, 50%, 60%, 70%, 80% or 90% relative to a native control plant, plant part or cell lacking the RAR1 expression cassette.

BIOLOGICAL DEPOSITS

The following vector molecules have been deposited under the terms of the Budapest Treaty with the Agricultural Research Service Culture Collection (NRRL), 1815 North University Street, Peoria, Ill. 61604, USA on the dates indicated. All restrictions on the availability of the biological deposits made in the instant application under the terms of the Budapest Treaty on the International Recognition of the Deposit of Microorganisms for the Purposes of Patent Procedure will be irrevocably removed upon granting of the patent.

Plasmid pNOV6605 was deposited with NRRL on Nov. 8, 2002 having Accession No. NRRL B-30635.

Plasmid pNOV5352 was deposited with NRRL on Nov. 8, 2002 having Accession No. NRRL B-30636.

Plasmid p11182 was deposited with NRRL on Nov. 8, 2002 having Accession No. NRRL B-30637.

These deposits were made merely as a convenience for those skilled in the art and are not an admission that a deposit is required under 35 USC § 112.

The invention will be further described by reference to the following detailed examples. These examples are provided for purposes of illustration only, and are not intended to be limiting unless otherwise specified.

EXAMPLES

Standard recombinant DNA and molecular cloning techniques used here are well known in the art and are described by J. Sambrook, et al., *Molecular Cloning: A Laboratory Manual*, 3d Ed., Cold Spring Harbor, N.Y.: Cold Spring Harbor Laboratory Press (2001); by T. J. Silhavy, M. L. Berman, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, New York, John Wiley and Sons Inc., (1988), Reiter, et al., *Methods in Arabidopsis Research*, World Scientific Press (1992), and Schultz et al., *Plant Molecular Biology Manual*, Kluwer Academic Publishers (1998).

Example 1

Identification of the RAR1 Nucleic Acid Molecule (cDNA) from Rice

The barley RAR1 protein was used as a query against the Syngenta proprietary rice genomic sequence database, using the TblastN algorithm and the Blosum 62 matrix with default settings (gap opening penalty=11; gap extension penalty=1). A single high scoring hit (bits=124; e value=1e-43) was identified, with a single uninterrupted open reading frame. The next highest scoring hit had a much lower e value=6e-12. Based on these results, we concluded that RAR1 is a single copy gene in rice, and the highest scoring hit was designated OsRAR1.

| Gene | SEQ ID NO: | Function and Similar Gene | E value | Homolog Reference and % homology |
|---|---|---|---|---|
| RAR1 | 1–2 | RAR1 CHORD domain protein from barley (Hordeum vulgare). Mutant is enhanced disease susceptible in specific plant R gene/ pathogen avr gene interactions | 1.00E-109 | Shirasu et al., Cell 99 (4) 355–366 (1999) 183/238 (76%) |

Example 2

Cloning and Sequence of Nucleic Acid Molecules from Rice

Primers designed based on the OsRAR1 genomic sequence were used to PCR amplify the full-length cDNA (start to stop codon) from first strand cDNA prepared from rice cultivar Nipponbare leaf tissue. The 5' to 3' primer sequences, with the ATG and TGA (reverse complement) were:

```
RAR1-ATG    AAGACGAAGATGTCGACGGAGGC      (SEQ ID NO:3)

RAR1-TGA    TCATGCGGCATCAGCATTGTG        (SEQ ID NO:4)
```

The PCR fragment was cloned into pCR2.1-TOPO per the manufacturer's instructions (Invitrogen), and several individual clones were subjected to sequencing analysis.

DNA preps for 2–4 independent clones were miniprepped following the manufacturer's instructions (Qiagen). DNA was subjected to sequencing analysis using the BigDye™ Terminator Kit according to manufacturer's instructions (ABI). Sequencing made use of primers designed to both strands of the predicted OsRAR1 gene. All sequencing data were analyzed and assembled using the Phred/Phrap/Consed software package (University of Washington) to an error ratio equal to or less than $10^{-4}$ at the consensus sequence level.

The OsRAR1 consensus sequence from the sequencing analysis was validated as being intact and the correct gene in several ways. The coding region was checked for being full length (predicted start and stop codons present) and uninterrupted (no internal stop codons). Alignment with the gene prediction and BLAST analysis was used to ascertain that this was in fact OsRAR1. Several correct clones were isolated.

Example 3

Insertion of RAR1 into Expression Vector and Transformation of Plants

Figure 2:
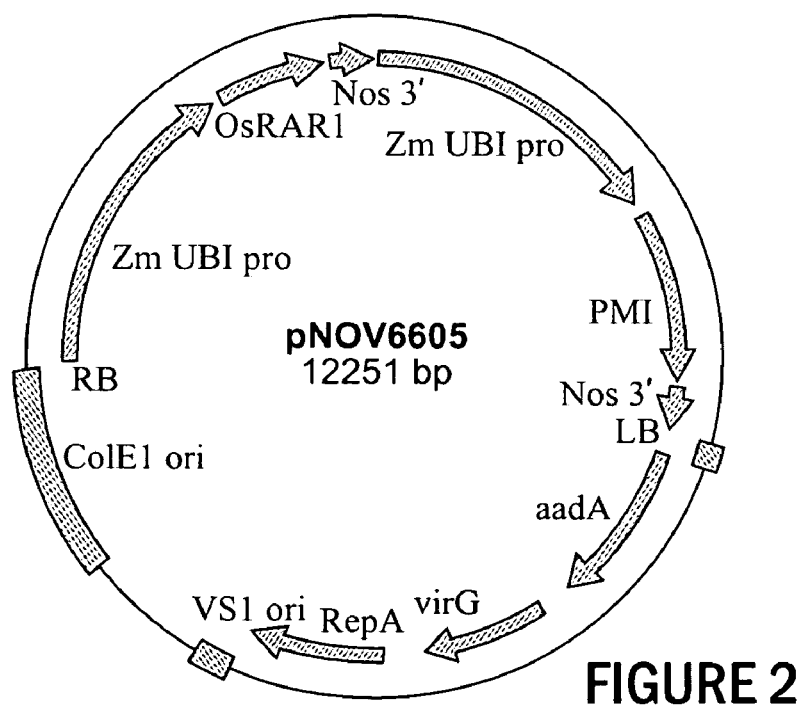
FIG. 2 is a map of plasmid pNOV6605.

A validated rice RAR1 cDNA (SEQ ID NO: 1) in pCR2.1-TOPO was subcloned using conventional restriction enzyme-based cloning into a vector, downstream of the maize ubiquitin promoter and intron, and upstream of the *Agrobacterium tumefaciens* Nos 3' end transcriptional terminator. The resultant OsRAR1 gene expression cassette (promoter, OsRAR1 and terminator) was further subcloned, using conventional restriction enzyme-based cloning, into the pNOV2117 binary vector, generating pNOV6605 (FIG. 2).

The pNOV6605 binary vector is designed for transformation and over-expression of OsRAR1 in monocots. It consists of a binary backbone containing the sequences necessary for selection and growth in *Escherichia coli* DH-5α (Invitrogen) and *Agrobacterium tumefaciens* LBA4404, including the bacterial spectinomycin antibiotic resistance aadA gene from *E. coli* transposon Tn7, origins of replication for *E. coli* (ColE1) and *A. tumefaciens* (VS1), and the *A. tumefaciens* virG gene. In addition to the binary backbone, pNOV2117 contains the T-DNA portion flanked by the right and left border sequences, and including the Positech™ (Syngenta) plant selectable marker and the OsRAR1 gene expression cassette. The Positech™ plant selectable marker confers resistance to mannose and in this instance consists of the maize ubiquitin promoter driving expression of the PMI (phosphomannose isomerase) gene, followed by the cauliflower mosaic virus 35S gene transcriptional terminator.

pNOV6605 was transformed into a rice cultivar (Kaybonnet) using *Agrobacterium*-mediated transformation, and mannose-resistant calli were selected and regenerated. Expression of OsRAR1 in 23 independent transgenic $T_0$ plants was analyzed by quantitative reverse transcription PCR (QRT-PCR). Raw data was normalized to QRT-PCR expression of an endogenous gene in these plants. In the transgenic OsRAR1 $T_0$ plants, expression of OsRAR1 mRNA ranged from equivalent to the wildtype (no increase in expression), to 59-fold greater than wildtype OsRAR1 mRNA levels by this assay (see Table 1 below)

TABLE 1

| OsRAR1 mRNA expression measured by QRT-PCR | |
|---|---|
| LINE REFERENCE | Fold Increased Expression |
| 4646 | 5x |
| 4653 | 18x |
| 4668 | 13x |
| 4687 | 10x |
| 4693 | ND (not determined) |
| 4696 | 59x |
| 4697 | 23x |
| 4698 | 7x |
| Wildtype | 1x |

Additional rice cultivars, such as but not limited to, Nipponbare and Taipei 309 are also transformed with a construct designed to overexpress the RAR1 gene product. Disease resistance is tested against a number of rice pathogens and races that are known to those skilled in the art, such as but not limited to, rice bacterial blight disease and rice blast disease as described below.

Example 4

Complementation Testing by Transformation of *Arabidopsis* RAR1 Mutant

An *Arabidopsis thaliana* RAR1 mutant is isolated and identified, as previously described (Warren et al. (1999) Genetics 152:401–412; Tornero et al. (2002) Plant Cell 14:1005–1015). The mutant is transformed with the rice RAR1 gene in a dicot overexpression vector as described in Example 3 or in the detailed description. Complementation of the *Arabidopsis* mutant by the rice RAR1 transgene is observed and analyzed.

Example 5

Gene Silencing or Under-Expression of Rice RAR1 Gene

Figure 3:
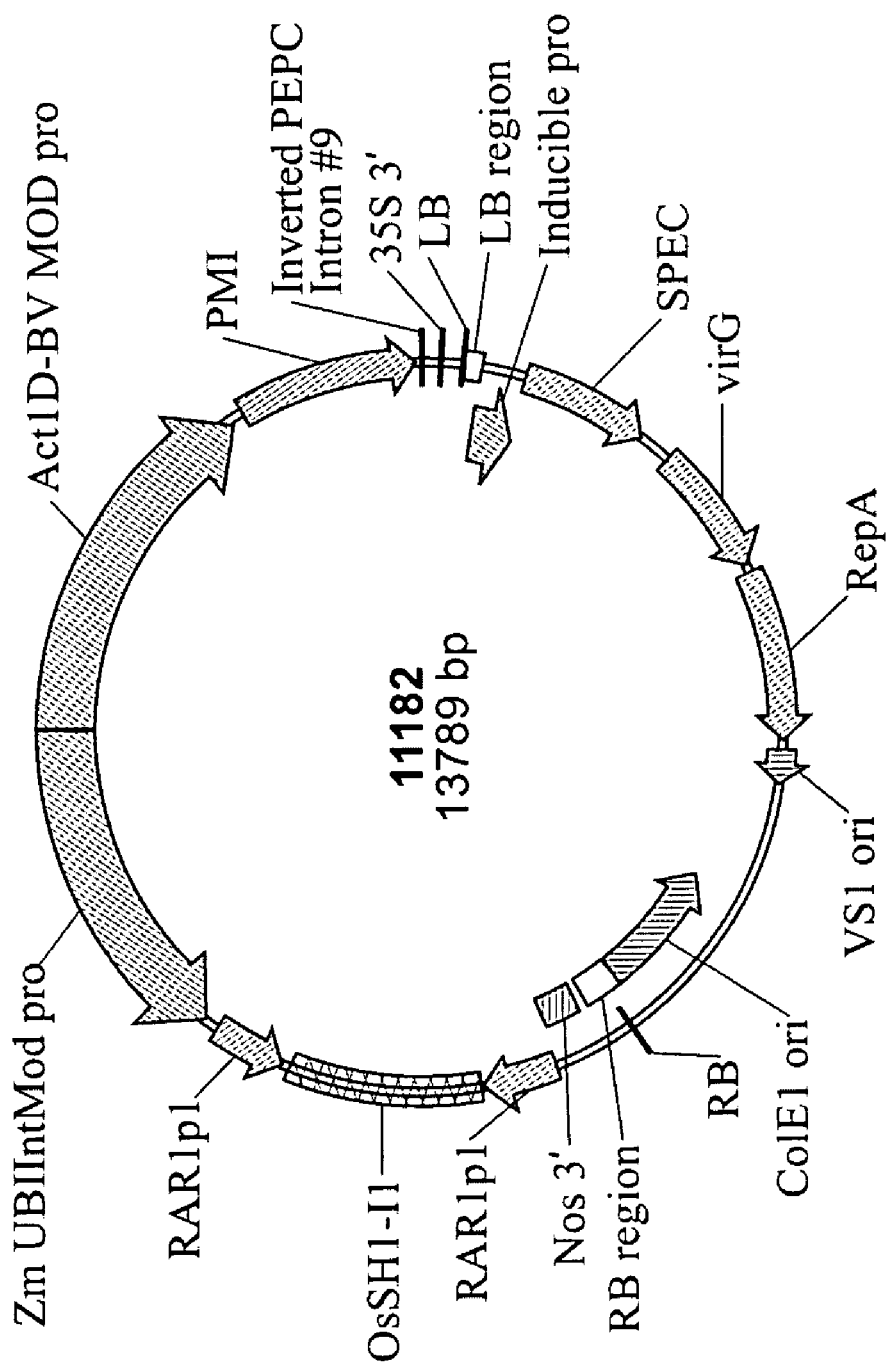
FIG. 3 is a map of plasmid p11182.

Rice cultivar(s) such as Kaybonnet are transformed by *Agrobacterium*-mediated transformation with an antisense construct of the Rice RAR1 gene, pNOV5352 (FIG. 1), or a dsRNA interference construct using a rice RAR1 gene fragment in sense and antisense, 11182 (FIG. 3). For the plant selectable marker gene, PPI, plasmids pNOV5352 and p11182 each use a modified rice actin1-gene promoter (Act1D-BV MOD pro—see FIGS. 1 and 3). For the RAR1 gene construct, plasmids pNOV5352 and p11182 each use an modified maize ubiquitin promoter (Zm UBIIntMod pro) that has been modified to remove unwanted restriction enzyme sites (see FIGS. 1 and 3). In pNOV5352, the gene of interest portion consists of a 449 bp segment of the OsRAR1 cDNA in the reverse or antisense orientation relative to the corresponding promoter and terminator. Finally, in 11182 the modified maize ubiquitin promoter is followed by the 449 bp OsRAR1 cDNA fragment (RAR1p1) in the sense orientation, then by the first intron of the rice shrunken1 gene (OsSH1-I1), then by the same OsRAR1 cDNA fragment (RAR1p1) in the antisense orientation, and finally by the Nos 3' terminator. Thus pNOV6605 is designed for overexpression of the OsRAR1 mRNA, whereas pNOV5352 and 11182 are designed for knockdown of OsRAR1 mRNA expression by antisense and double-stranded RNA methodologies, respectively. Another difference between the different OsRAR1 plasmids is the relative orientation of the selectable marker and gene of interest cassettes in the T-DNA portion. In pNOV6605, the order of components is right T-DNA border, gene of interest cassette in forward orientation (promoter, OsRAR1 cDNA and terminator) and selectable marker cassette in forward orientation (promoter, PMI cDNA and terminator), followed by the left T-DNA border (FIG. 2). In pNOV5352 and 11182, the order is right T-DNA border, gene of interest cassette in reverse orientation (terminator, knockdown portion, and promoter), followed by the selectable marker cassette in forward orientation (promoter, PMI cDNA and terminator), and finally the left T-DNA border (FIGS. 1 and 3).

Inhibition or silencing, or under-expression of the RAR1 gene is observed and analyzed by methods such as, but not limited to, Northern blot analysis, Western blot analysis, or disease resistance bioassays (such as those set forth below in the Examples). Disease susceptibility to a variety of rice pathogens and races is observed.

Assays for testing disease resistance to a variety of pathogens known to those skilled in the art are performed on transgenic plants and non-transgenic parental lines to determine alteration in disease resistance.

For example, but by no means limiting, such disease resistance assays are performed essentially as described below.

Example 6

Rice Detached Leaf Assay for Bacterial Blight

This example describes the disease resistance assay of the RAR1 transformed rice plants and control plants using the detached leaf assays for bacterial blight (*Xanthomonas oryzae pv oryzae* (Xoo or *Xanthomonas*; mixture of isolates XOO698 and PXO112)). Transgenic plants were also compared to resistance of rice plants treated with Bion™, and wildtype Kaybonnet.

1. Rice seedlings were planted 1 seed per pot in 4 cm×4 cm pots with a mix of 50% peat and 50% John Innes Potting compost number 3 soil. Plants were checked twice daily and spot watered if soil appears dry on the surface. Plants were grown in a growthroom (16 hour light cycle at a light intensity of 15000 μMol; 27° C. day 80% humidity; 20° C. night 90% humidity) until testing.
2. Plants treated with Bion™ (formulation type and strength e.g. azibenzolar-s-methly 800 g/kg wettable powder) were subjected to soil drench application 7 days prior to inoculating with bacteria. The 4 cm×4 cm pots have a volume of 40 ml with a headspace of 4 ml for the solution. Thus, applying a 600 ppm solution to the top of the plants in the pots will result in a 60 ppm treatment. A 600 ppm solution comprises 60 mg active ingredient in 100 ml water. Dilutions from this solution are made for treatments with lower concentrations. Prior to application of Bion™, the plants to be treated are placed in saucers 2 cm deep and are not watered 24 hours pre treatment. The Bion™ application was made by pipetting 40 ml of the chemical solution onto the surface of the soil in each pot. After 24 hours post treatment the saucers were removed and normal watering regime is restored
3. Xoo cultures for inoculation were produced from single isolate bacterial stocks (kept at 4° C. stored on) 2 days prior test date. Xoo bacterial cultures were grown in 500 ml nutrient broth. Bacteria were picked up on the tip of a sterile pipette and resuspended in 500 ml nutrient broth (recipe below). Cultures were incubated at 25° C. on a platform shaker (115 rpm) for between 1 and 4 days (typically flasks are used 2 days after introduction of the bacteria). Successful bacterial growth was indicated by the nutrient broth becoming opaque and a more intense yellow colour. Immediately before inoculation of leaf pieces flasks of Isolates XOO698 (JH code K4214) and PXO112 (JH code K4211) were mixed to produce a dual isolate inoculation.
4. For the *Xanthomonas* detached leaf assay, plants approximately 12 weeks old are used. A total of 15 leaf samples were cut from randomly selected plants of each line of interest (i.e. transgenic event or non transgenic germplasm), or each individual treatment (i.e. combination of line and chemical application). A leaf sample is a section of the leaf between 5 cm and 6 cm long, and the width of the leaf wide, and may include the tip of the leaf. Multiple leaf samples can be obtained from one leaf. Leaf samples are always taken from the youngest fully expanded leaf available on the plant.

Control lines and treatments were included consisting of leaf 30 leaf samples from 12 week old non-transgenic (wildtype) plants of the same variety as that used in the generation of the transgenic events and 30 leaf samples from Bion™ treated wildtype plants (12-week-old). As some level of senescence regularly occurs in detached leaf assays further plates of leaves that were only inoculated with nutrient broth (i.e. uninoculated controls) were also prepared. These plates consist of 30 leaf samples from wildtype plants, 30 leaf samples from Bion™ treated wildtype plants and 15 leaf samples from 2 transgenic lines selected at random. These control plates allow assessors to clearly establish the difference in appearance between disease symptomology and unrelated senescence in the leaf samples.

5. Leaf samples were placed adaxial side up onto petri dishes containing 1% tap water agar amended with 75 ppm benzimidazole. Leaf samples were fully randomised between plates with a maximum of 6 samples per plate.
6. Leaf samples were inoculated individually with a syringe by twice injecting approximately 0.1 ml of Xoo (isolates XOO698 mixed with PXO112) bacterial culture solution into the tip end of the leaf sample (one injection either side of the vascular bundle). Inoculations were completed in a laminar flow hood to reduce contamination of the bacterial cultures. After inoculation the plates were placed into a controlled environment incubator with conditions set at 32° C. day, 25° C. night and a 16 hour light cycle. A maximum humidity of 90% was maintained in the cabinet throughout the plate incubation time.

Assessments of disease development and senescence levels were completed every 48 hours, for up to 10 days after inoculation. Assessments made after 2 days for "spontaneous suicide" and every 3 days for curl, health and levels of "ooze." The key indication of disease establishment within the leaf sample was the presence of yellow bacterial exudates (ooze) at one or both cut ends of the leaf. Lower incidence of exudates was a measure of decreased disease development and, hence enhanced disease resistance and in the line(s) of interest resistance within the leaf sample.

Recipes

Nutrient Broth for *Xanthomonas Oryzae pv Oryzae* Inoculum Production 6.5 g Nutrient Broth (Oxoid CM1) into 500 ml Demonized Water. Stir until fully dissolved (about 5 minutes). Autoclave at 121° C. for 20 minutes.

Results of this assay are summarized below and in Table 2.

The data for the blight assay was collated from the levels of ooze that were observed on the leaf pieces. Ooze is a symptom of *Xanthomonas* infection documented as occurring in detached leaf assays and is based on a method described by G. L. Xie (Plant Disease 82:1007–1011 (September 1998). Ooze manifests as a yellow exudate that occurs at the cut ends of an infected leaf. Leaf pieces were scored differently depending on if the ooze was observed at the inoculated end only or if the ooze had developed through the leaf and was also present at the opposing end of the leaf to the end innocuated. It was assumed that if ooze was observed at both ends, the leaf sample was exhibiting no resistance to the disease. If the inoculated end only exhibited ooze, there was some indication that the leaf piece was showing some resistance to the disease. If no ooze was observed at either end of the leaf piece there is an indication of strong resistance to the disease. Leaf pieces were scored as having presense or absense of ooze at each end (no quantification of the amount of ooze present).

The data indicates that although there are no lines that are totally free of the disease, there are lines that show a much lower level of disease than the wildtype control. Six of the nine transgenic OsRAR1 lines assayed (4646, 4668, 4687, 4693, 4696 and 4697) showed increased resistance to *Xanthomonas* compared to the wildtype Kaybonnet rice. Lines 4653 and 4698 appeared to have no increased resistance to *Xanthomonas*. The Bion™ treated plants included in this test as a control failed to show increased resistance, but other controls behaved as expected. A small number of replicates senesced at an accelerated rate, and were totally chlorotic 48 hours after test set up. These replicates were not limited to any single line or treatment, and were treated as an anomaly and excluded from the test.

Example 7

Rice Assay for Rice Blast Disease (Caused by *Pyricularia Grisea*; Also Known as *Magnaporthe Grisea*)

This example describes the bioassay for resistance of RAR1 transgenic rice to rice blast *Pyricularia* grisea (strain K4005).

1. Rice seedlings were planted 1 seed per pot in 4 cm×4 cm pots with a mix of 50% peat and 50% John Innes Potting compost number 3 soil. Plants were checked twice daily and spot watered if soil appears dry on the surface. Plants were grown in a growthroom (16 hour light cycle at a light intensity of 15000 µMol; 27° C. day 80% humidity; 20° C. night 90% humidity) until testing.
2. Plants treated with Bion, were treated using a drench application 7 days prior to inoculation. The 4 cm×4 cm diameter pots have a volume of 150 mls with a headspace of 15 mls for the solution. Thus, applying a 600 ppm solution to the top of the plants in the pots will result in a 60 ppm treatment. A 600 ppm solution is made up of 60 mg active ingredient in 100 ml water. Make dilutions from that solution for treatments with lower concentrations.
3. *Pyricularia grisea* inoculum was prepared from 5 day old single isolate stock plates (kept at 25° C. on rice leaf extract agar—recipe below) immediately before required for inoculation. 20 ml sterile deionised water was added to a plate of *Pyricularia grisea*, which is then rubbed with a small soft brush to encourage the spores into solution. The resulting spore and mycelium solution was then filtered through one layer of fine mesh muslin. Spores were counted in with using haemocytometer and the inoculum solution was diluted to produce a concentration of 200,000 spores/ml. The inoculum was used within one hour of production. It is recommended to allow 5 ml of inoculum per plate. Rice leaf extract agar for *Pyricularia* inoculum production: 45 g Czapek Dox Agar, 10 g Oxide Agar No. 3, 1000 ml rice leaf extract. Extract 50 g of dried straw with 1000 ml of water at 100° C. for 1 hour. Autoclave at 121° C. for 20 minutes.

For the *Pyricularia grisea* detached leaf assay plants approximately 12 weeks old were used. A total of 15 leaf samples were cut from randomly selected plants of each line of interest (i.e. transgenic event or non transgenic germplasm), or each individual treatment (i.e. combination of line and chemical application). A leaf sample was a section of the leaf between 5 cm and 6 cm long, and the width of the leaf wide, and may include the tip of the leaf. Leaf pieces were placed so that both ends of the leaf were buried into the agar as this increases the green life of the leaf samples. Multiple leaf samples can be obtained from one leaf. Leaf samples were always taken from the youngest fully expanded leaf available on the plant. Control lines and treatments were included consisting of leaf 30 leaf samples from 12 week old non-transgenic (wildtype) plants of the same variety as that used in the generation of the transgenic events and 30 leaf samples from Bion™ treated wildtype plants (12 weeks old). As some level of senescence regularly occurs in detached leaf assays further plates of leaves that were inoculated with only sterile deionized water (i.e. uninoculated controls) were also prepared. These plates consisted of 30 leaf samples from wildtype plants, 30 leaf samples from Bion™ treated wildtype plants and 15 leaf samples from 2 transgenic lines selected at random. These control plates allow assessors to establish clearly the difference in appearance between disease symptomology and unrelated senescence in the leaf samples.

5. Leaf samples were placed adaxial surface upwards onto petri dishes containing 1% tap water agar amended with 75 ppm benzimidazole. Leaf samples were fully randomised between plates with a maximum of 6 samples per plate.
6. Inoculum was sprayed onto the plates using a Devilbiss spray gun. Leaf pieces were sprayed to produce an equal coverage of droplets over the exposed leaf surface. The petri dish plate lids were replaced immediately and plates were incubated in a controlled environment cabinet for up to 8 days (conditions–14 hour light cycle; 24° C. day; 24° C. night constant 90% humidity).
7. Plates were assessed for disease development (expressed as a estimated % disease coverage) and senescence levels every 48 hours for up to 8 days.

Results for bacterial blight and blast assays on OsRAR1 transgenic plants are set forth below in Table 2. For each independent OsRAR1 transgenic $T_1$ line, the number of individual plants is shown in parentheses next to the line designation; 12 wildtype (Kaybonnet) plants were used. The plants used in this assay are the putatively selfed progeny of $T_0$ plants containing at least one copy of the selectable marker gene due to germination on mannose. Under these conditions plants not expressing the PMI transgene turn brown and die. However, the plants assayed varied from being genetically hemizygous for the transgene to having multiple transgene copies, as determined by segregation ratios on mannose media and Taqman™ copy number determination (data not shown). Expression data for the $T_0$ parents of these OsRAR1 transgenic plants was determined by quantitative RT-PCR as shown above in table 1.

The data from the rice blast assay are also set forth in Table 2 below. Six of the nine transgenic OsRAR1 lines assayed (4646, 4653, 4668, 4687, 4693 and 4700) showed less disease coverage than the wildtype Kaybonnet rice line, demonstrating enhanced disease resistance in these lines. Importantly, four of the nine lines (4646, 4668, 4687 and 4693) showed enhanced resistance to both blight and blast. Two lines showed enhanced resistance only to blight (4696 and 4697) or to blast (4653 and 4700). Transgenic line 4697 did not show any increase in disease resistance and had similar disease coverage as the wildtype. The wildtype treated with Bion™ showed the expected effect of decreased disease coverage.

This data clearly demonstrates that overexpression of the RAR1 gene in transgenic plants enhances disease resistance.

TABLE 2

Results of Disease Resistance Bioassays

| LINE REFERENCE | Xanthomonas oryzae % No Ooze | % Ooze Inoculated end | % Ooze both ends | Pyricularia grisea % Disease Coverage |
|---|---|---|---|---|
| 4646 (13) | 38.5 | 30.8 | 30.8 | 7.7 |
| 4653 (14) | 7.1 | 7.1 | 85.7 | 6.1 |
| 4668 (7) | 46.7 | 26.7 | 26.7 | 6.5 |
| 4687 (11) | 46.7 | 33.3 | 20.0 | 7.3 |
| 4693 (8) | 78.6 | 7.1 | 14.3 | 8.7 |
| 4696 (17) | 50.0 | 28.6 | 21.4 | 14.6 |
| 4697 (10) | 46.7 | 20.0 | 33.3 | 23.3 |
| 4698 (20) | 21.4 | 7.1 | 71.4 | 12.0 |
| 4700 (12) | 35.7 | 14.3 | 50.0 | 6.9 |
| Uninoculated Kaybonnet wt | 100.0 | 0.0 | 0.0 | 0.0 |
| Uninoculated 4698 | 100.0 | 0.0 | 0.0 | 0.0 |
| Uninoculated *4696* | 100.0 | 0.0 | 0.0 | 0.0 |
| Uninoculated BION KAYBONNET | 100.0 | 0.0 | 0.0 | 0.0 |
| Inoculated Kaybonnet wt | 3.6 | 35.7 | 60.7 | 24.7 |
| Inoculated Kaybonnet wt + BION 200 ppm | 20.0 | 13.3 | 66.7 | 6.3 |

Example 8

Transformation of Wheat with Rice RAR1 Expression Cassette

Avalidated rice RAR1 cDNA (SEQ ID NO:1) is subcloned into expression vectors suitable for expression in wheat. The vectors used for wheat transformation by biolistic bombardment have the same gene expression cassettes as those used for rice *Agrobacterium tumefaciens*-mediated transformation, except these are in the context of an ordinary pUC-based plasmid backbone rather than the binary vector backbone used for rice. These pUC-based vectors are co-bombarded with a vector containing the same plant selectable marker cassette (modified rice actin1 promoter (Act1D-BV MOD pro), PMI gene and CaMV 35S 3' terminator) present in the rice binary vectors described above in Example 3, except that this selectable marker cassette is in a pUC-based vector backbone. Expression of the OsRAR1 mRNA is analyzed bo QRT-PCR as described above.

Example 9

*Puccinia Triticina* (Leaf Rust) Assays

1. The detached leaf sandwich method, (adapted from Arraiano, Brading and Brown, (2001) "A detached seedling leaf technique to study resistance to *Mycosphaerella graminicola* (anamorph *Septoria triticl*) in wheat", Plant Pathology 50:339–346) was followed as described below. Under aseptic conditions, two strips of agar are cut from 10 $cm^2$ square petri dishes containing 0.4% (w/v) tap water agar (TWA) plates leaving a 3.5 cm gap down the middle of the plates. Leaf pieces (length=5 cm) are taken from the top and bottom of each fully expanded leaf to be tested. The strips of agar are laid longitudinally along the borders of the gap, while the leaf pieces are placed horizontally across the gap (adaxial surface upwards), and tucked in between the double layer of agar. The first and second fully expanded leaves from each transgenic plant are used.
2. Plates are then sprayed with 0.05% (v/v) Tween-20 using a Devilbiss hand spray gun at 10 PSI. Following this, 50 mg of *Puccinia triticina* spores are weighed into plastic boats, sieved through muslin onto another plastic boat and then 'puffed' onto the DLA's via a settling tower at 4 PSI. The tower is left in place for 2 minutes before the plates are removed.
3. The plates are then incubated at 21° C. day, 17° C. night, in the dark for 24 h. Following this they are incubated at 21° C. day, 17° C. night, 16 h daylength, 60% RH, and % disease cover is assessed at 8 and 12 dpi.
4. *Puccinia triticina* is maintained on whole plants and is transferred onto uninfected 10 d old plants every 10 days. Inoculated plants are maintained at 21° C. day, 17° C. night, 60% RH. Trangenic wheat plants expressing the OsRAR1 transgene show increased resistance.

Example 10

*Septoria Tritici* Assays

This example describes the assays to determine the resistance of transgenic and wildtype plants to *Septoria tritici.*

1. The detached leaf sandwich method, (adapted from Arraiano, Brading and Brown, 2001, supra) was followed as described in Example 9, section 1 above.
2. Detached leaf assay plates are inoculated with a suspension of $1\times10^6$ *Septoria tritici* spores/ml in 0.05% (v/v) Tween-20. The spore suspension is applied using a Devilbiss hand spray gun at 10 PSI. The plates are then incubated at 21° C. (16 h per 24 h), 17° C. (8 h per 24 h), 60% relative humidity (RH), in the dark for 48 h. Following this, the plates are incubated at 21° C. day, 17° C. night, 16 h daylength, 60% RH. The percent disease coverage is assessed at 17 days after innoculation.
3. *Septoria tritici* is cultured on CDV8 agar (Czapek Dox+V8 juice). Plates are incubated in the dark at 19° C. Subculturing is performed every 10 days by spore suspension transfer. Wheat plants expressing the OsRAR1 transgene show increased resistance to *Septoria.*

Example 11

*Blumeria Graminis Graminis* f. sp. *Tritici* (Wheat Powdery Mildew) Assays

This assay is to determine the disease resistance of OsRAR1 transgenic wheat lines and wildtype lines to wheat powdery mildew.
1. The detached leaf sandwich method, (adapted from Arraiano, Brading and Brown, 2001, supra) is followed as described in 9, section 1 above.
2. 16 h prior to inoculation several leaves from stock plants with approx. 70% powdery mildew coverage on each leaf were harvested, placed onto damp filter paper in a petri dish and incubated at 21° C. day, 17° C. night, 60% RH, 16 h daylength to encourage sporulation.
3. Detached leaf assay (DLA) plates are inoculated by using a pressurized air-line to blow spores from infected leaves into a settling tower and onto the plates. The spores are allowed to settle for 2 minutes before the tower is removed. The plates are then incubated at 21° C. (16 h per 24 h), 17° C. (8 h per 24 h), 60% RH, in the dark for 24 h. Following this, the plates are incubated at 21° C. day, 17° C. night, 16 h daylength, 60% RH. The percent disease coverage is assessed at 7 days after innoculation.

*Blumeria graminis* f. sp. tritici is maintained on whole plants and is transferred onto uninfected 10 d old plants every 7 days. Inoculated plants are maintained at approx. 21° C. Wheat plants expressing a OsRAR1 transgene show increased resistance to Blumeria.

The above-disclosed embodiments are illustrative. This disclosure of the invention will place one skilled in the art in possession of many variations of the invention. All such obvious and foreseeable variations are intended to be encompassed by the present invention. All references cited within are hereby incorporated by reference in their entirety.

---

What is claimed is:

1. A transgenic plant comprising an isolated nucleic acid molecule comprising a nucleotide sequence selected from the group consisting of:
   a) a nucleotide sequence encoding the amino acid sequence of SEQ ID NO: 2;
   b) a nucleotide sequence which is the reverse complement of (a).

2. The transgenic plant according to claim 1, wherein said nucleic acid molecule is operably linked to a promoter.

3. Transgenic progeny or seed from the transgenic plant of claim 1, wherein the transgenic progeny or seed comprises the nucleic acid molecule.

4. The transgenic plant of claim 1, wherein the nucleic acid molecule is expressed in epidermis, vascular tissue, meristem, cambium, cortex, pith, leaf, sheath, root, flower, developing ovule or seed.

5. The transgenic plant of claim 1, wherein the plant is selected from the group consisting of: rice, wheat, barley, rye, corn, potato, canola, soybean, sunflower, carrot, sweet potato, sugarbeet, bean, pea, chicory, lettuce, cabbage, cauliflower, broccoli, turnip, radish, spinach, asparagus, onion, garlic, eggplant, pepper, celery, squash, pumpkin, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum and sugarcane.

6. The transgenic plant of claim 5, wherein the plant is rice.

7. The transgenic plant of claim 1, wherein the plant is a monocot.

8. The transgenic plant of claim 7, wherein the monocot is selected from the group consisting of maize, wheat, barley, oats, rye, millet, sorghum, trticale, secale, einkorn, spelt, emmer, teff, milo, flax, gramma grass, Tripsacum, and teosinte.

9. The transgenic plant according to claim 1, wherein said nucleotide sequence comprises:
   a) the nucleotide sequence of SEQ ID NO: 1;
   b) a nucleotide sequence which is the reverse complement of (a).

10. Transgenic progeny or seed from the transgenic plant of claim 9, wherein the transgenic progeny or seed comprises the nucleotide sequence.

11. A method of enhancing resistance against pathogen or disease causing agent in a plant, comprising introducing an expression cassette comprising a nucleic acid molecule encoding the amino acid sequence of SEQ ID NO: 2 or an expression cassette comprising SEQ ID NO: 1 into the plant.

12. The method of claim 11, wherein the pathogen or disease causing agent is a nematode, bacteria, fungus, virus or viroid.

13. The method of claim 12, wherein the pathogen is selected from the group consisting of: *Xanthomonas* spp., *Psudomonas* spp., *Rhizoctonia* spp., *Magnaporthe* spp., *Pythium* spp., *Phytophthora* spp., *Fusarium* spp. *Sclerotinia* spp.

14. A plant produced by the method of claim 11, wherein the plant has enhanced pathogen or disease resistance.

15. A method of increasing expression of disease resistance genes in a plant, comprising introducing an expression cassette comprising a nucleic acid molecule encoding the amino acid sequence of SEQ ID NO: 2 or an expression cassette comprising SEQ ID NO: 1 into the plant.

* * * * *